US008329227B2

(12) United States Patent
Smith

(10) Patent No.: US 8,329,227 B2
(45) Date of Patent: Dec. 11, 2012

(54) COMPOSITIONS FOR IMPROVING MENTAL PERFORMANCE

(75) Inventor: Kyl L. Smith, Corinth, TX (US)

(73) Assignee: Factor Nutrition Labs, LLC, Portland, ME (US)

( * ) Notice: Subject to any disclaimer, the term of this patent is extended or adjusted under 35 U.S.C. 154(b) by 1010 days.

(21) Appl. No.: 10/519,515

(22) Filed: Dec. 7, 2004

(65) Prior Publication Data

US 2005/0244510 A1    Nov. 3, 2005

Related U.S. Application Data

(63) Continuation of application No. PCT/US02/21062, filed on Jul. 3, 2002.

(60) Provisional application No. 60/302,653, filed on Jul. 5, 2001.

(51) Int. Cl.
| A61K 31/683 | (2006.01) |
| A61K 31/685 | (2006.01) |
| A61K 33/26 | (2006.01) |
| A61K 33/32 | (2006.01) |
| A61K 33/34 | (2006.01) |

(52) U.S. Cl. ........ 424/725; 424/617; 424/630; 424/643; 424/646; 424/722; 424/766; 514/424; 514/52; 514/560; 514/78

(58) Field of Classification Search .......................... None
See application file for complete search history.

(56) References Cited

U.S. PATENT DOCUMENTS

| 3,433,875 A | * | 3/1969 | Denis et al. |
| 4,933,354 A | * | 6/1990 | Ikeguchi et al. |
| 6,117,853 A | * | 9/2000 | Sakai et al. |
| 2002/0182196 A1 | * | 12/2002 | McCleary |

FOREIGN PATENT DOCUMENTS

| CN | 1117823 A | * | 3/1996 |
| CN | 1222348 A | * | 7/1999 |
| RU | 2164764 C1 | * | 4/2001 |

OTHER PUBLICATIONS

Grioli, S et al. Fundamen. Clin. Pharmocol. (1990); 4(2: 169-173. Pyroglutamic acid improves the age associated memory impairment.*
Davis, BP et al. Journal or Manipulative & Physiological Therapeutics (1982); 5(3): 123-127. Enhanced absorption of oral vitamin B12 from a resin adsorbate administered to normal subjects.*
Grioli, S et al. Fundam. Clin. Pharmacol (1990); 4: 169-173. Pyroglutamic acid improves the age associated memory impairment.*
Cenacchi T, Bertoldin T, Farina C, Fiori MG, Crepaldi G. "Cognitive decline in the elderly: A double blind, placebo-controlled multicenter study on efficacy of phosphatidylserine administration." Aging Clin Exp Res, 5:123-133 (1993).
Crook TH, Tinklenberg J, Yesavage J, Petrie W, Nunzi MG, Massari DC. "Effects of phosphatidylserine in age-associated memory impairment." Neurology, 41:644-649 (1991).
Amaducci L, Crook TH, Lippi A, Bracco L, Baldereschi M, Latorraca S, Piersanti P, Tesco G, Sorbi S. "Use of phosphatidylserine in Alzheimer's disease." Annals NYAcadSci, 640:245-249 (1991).
Crook T, Petrie W, Wells C, Massari DC. "Effects of phosphatidylserine in Alzheimer's disease." Psychopharmacol Bull, 28:61-66 (1992).
Toffano G, Battistella A, Orlando P. "Pharmacokinetics of radiolabelled brain phosphatidylserine." Clin Trials J, 24:18-24 (1987).
Nishizukay. "Turnover of inositol phospholipids and signal transduction." Science, 225:1365-1370 (1984).
Cohen SA, Muller WE. "Age-related alterations of NMDA-receptor properties in the mouse forebrain: Partial restoration by chronic phosphatidylserine treatment." Brain Res, 584:174-180 (1992).
Ball MJ. "Neuronal loss, neurofibrillary tangles and granulovacuolar degeneration in the hippocampus with ageing and dementia. A quantitative study." Ada Neuropath, 37:111-118 (1977).
Scheibel ME, Lindsay RD, Tomiyasu U, Scheibel AB. "Progressive dendritic changes in the aging human limbic system." Exptl Neurol, 53:420-430 (1976).
Lippaas, Critchettdj, Ehlertf, Yamamurahi, Ennasj, Bartusrt. "Age-related alterations in neurotransmitter receptors: An electrophysiological and biochemical analysis." Neurobiol Aging, 2:3-8.(1981).
Pepeu G, Spignoli G. "Nootropic drugs and brain cholinergic mechanisms." Prog Neuro-Psychopharmacol Biol Psychiat, 13 :S77-S88 (1989).
Bartus RT, Dean RL, Beer B, Lippa AS. "The cholinergic hypothesis of geriatric memory dysfunction." Science, 217:408-417 (1982).
Petersen RC, Jack CR, Jr, Xu YC, Waring SC, O'Brien PC, Smith GE, Ivnik RJ, Tanglos EG, Boeve BF, Kokmen E. "Memory and MRI-based hippocampal volumes in aging and AD." Neuro,54:581-587 (2000).
Corwin J, Dean RL, Bartus RT, Rotrosen J, Watkins DL. "Behavioral effects of phosphatidylserine in the aged Fischer 344 rat: Amelioration of passive avoidance deficits without changes in psychomotor task performance." Neurobiol of aging, 6:11-15 (1985).
Zanotti A, Aporti F, Toffano G, Valzelli L. Effects of phosphatidylserine on avoidance relearning in rats. Pharmacol Res Commun, 16:485-493 (1984).
Drago F, Canonico PL, Scapagnini U. "Behavioral effects of phosphatidylserine in aged rats." NeurobiolAging 2:209-213 (1981).
Aporti F, Borsato R, Calderini G, Rubini R, Toffano G, Zanotti A, Valzelli L, Goldstein L. "Age-dependent spontaneous EEG bursts in rats: Effects of brain phosphatidylserine." Neurobiol Aging, 7:115-120 (1986).

(Continued)

Primary Examiner — Michele C. Flood
(74) Attorney, Agent, or Firm — Perkins Coie LLP

(57) ABSTRACT

The present invention provides formulas for producing compositions for the structural/functional nutritional support for those who struggle with poor focus, concentration and/or memory. In addition, the present invention provides compositions comprising nutritional/botanical factors helpful to those who subjectively experience transient mental fatigue or poor cognitive function. The compositions of this invention consist primarily of the following ingredients B-complex vitamins, antioxidants, minerals, phosphatidyl serine (PS), choline, dimenthyl-aminoethanol (DMAE), docosa-hexaenoic acid (DHA), L-pyroglutamic acid, as well as herbal extracts from Bacopa monniera, Vinca minor, and Huperzia serrata. The present invention also relates to the administration of these compounds to alleviate mental fatigue or poor cognitive function.

18 Claims, No Drawings

OTHER PUBLICATIONS

Zanotti A, Valzelli L, Toffano G. "Chronic phosphatidylserine treatment improves spatial memory and passive avoidance in aged rats." *Psychopharmacol*, 99:316-321 (1989).

Casamenti F, Mantovani P, Amaducci L, Pepeu G. "Effect of phosphatidylserine on acetylcholine output from the cerebral cortex of the rat." *J Neurochem*, 32:529-533 (1979).

Nunzi MG, Milan F, Guidolin D, Toffano G. Dendritic "Spine loss on hippocampus of aged rats. Effect of brain phosphatidylserine administration." *Neurobiol Aging*, 8:501-510 (1987).

Nunzi MG, Milan F, Guidolin D, Polato P, Toffano G. "Effects of phosphatidylserine administration on age-related structural changes in the rat hippocampus and septal complex." *Pharmacopsychiat*, 22:125-128 (1989).

Heiss W-D, Szelies B, Kessler J, Herholz K. "Abnormalities of energy metabolism in Alzheimer's disease studied with PET." *Annals NYAcad Sci*, 640:65-71 (1991).

Villardita C, Grioli S, Salmeri G. Nicoletti F, Pennisi G. "Multicentre clinical trial of brain phosphatidylserine in elderly patients with intellectual deterioration." *Clin Trials J*, 4:84-93 (1987).

Palmieri G, Palmieri R, Inzoli MR, Lombardi G, Sottini C, Tavolato B, Giometto B. "Double-blind controlled trial of phosphatidylserine in patients with senile mental deterioration." *Clin Trials J*, 24:73-83 (1987).

Amaducci L. "Phosphatidylserine in the treatment of Alzheimer's disease: Results of a multicenter study." *Psychopharmacol Bull*, 24:130-134 (1988).

Delwaide PJ, Gyserynck-Mambourg AM, Hurlet A, Ylieff M. "Double-blind randomized controlled study of phosphatidylserine in senile demented patients." *Acta Neurol Scand*, 73:136-140 (1986).

Engel RR. "Double-blind cross-over study of phosphatidylserine vs. placebo in subjects with early cognitive deterioration of the Alzheimer type." *Eur Neuropsychopharmacol*, 2:149-155 (1992).

Schreiber S, Kampf-Sherf O, Gorfine M, Kelly D, Oppenheim Y, Lerer B. "An open trial of plant-source derived phosphatidylserine for treatment of age-related cognitive decline." *Isr J Psychiatry Relat Sci*, 37:302-307 (2000).

Maggioni M, Picotti GB, Bondiolotti GP, Panerai A, Cenacchi T, Nobile P, Brambilla F. "Effects of phosphatidylserine therapy in geriatric patients with depressive disorders." *Acta Psychiatr Scand*, 81:265-270 (1990).

Cenacchi T, Baggio C, Palin E. "Human tolerability of oral phosphatidylserine assessed through laboratory examinations." *Clin Trials J*, 24:125-131 (1987).

Heiss WD. "Long-term effects of phosphatidylserine, pyritinol, and cognitive training in Alzheimer's disease." *Cognitive Deterioration*, 5:88-98 (1994).

Sinforiani E, Agostinis C, Merlo P, Gualtieri S, Mauri M, Mancuso A. "Cognitive decline in ageing brain. Therapeutic approach with phosphatidylserine." *Clin Trials Jim*,24:115-125, (1987).

Granata Q, Dimichele J. "Phosphatidylserine in elderly patients. An open trial." *Clin Trials J*, 24:99-103 (1987).

Allegro L, Favaretto V, Ziliotto G. "Oral phosphatidylserine in elderly patients with cognitive deterioration. An open study." *Clin Trials J*, 24:104-108 (1987).

Caffara P, Santamaria V. "The effects of phosphatidylserine in patients with mild cognitive decline. An open trial." *Clin 7Wa/s./*, 24:109-1 14 (1987).

Rosadini G, Sannita WG, Nobili F, Cenacchi T. "Phosphatidylserine: Quantitative EEG effects in healthy volunteers." *Neuropsychobiol*, 24:42-48 (1990-1991).

Heiss W-D, Kessler J, Slansky I, Mielke R, Szelies B, Herholz K. "Activation PET as an instrument to determine therapeutic efficacy in Alzheimer's disease." *Annals NYAcad Sci*, 695:327-331 (1993).

Filburn CR. "Dietary supplementation with phospholipids and docosahexaenoic acid for age-related cognitive impairment." *J Am Nutraceutical Assoc*, 3:45-55 (2000).

Pevet P, Buijs RM, Masson-Pevet M. "Effect of pinealectomy and a constant high level of circulating melatonin or of 5-methoxytryptamine on the vasopressinergic innervation in the brain of the European hamster (*Cricetus cricetus*, L)." *J Neural Transm*, 70:287-294 (1987).

Klinkhammer P, Szelies, Heiss W-D. "Effect of phosphatidylserine on cerebral glucose metabolism in Alzheimer's disease." *Dementia*, 1:197-201 (1990).

Latorraca S, Piersanti P, Resco G, Piacentini S, Amaducci L, Sorbi S. "Effect of phosphatidylserine on free radical susceptibility in human diploid fibroblasts." *J Neural Transm*, 6:73-77 (1993).

Colodny L, Hoffinan RL. "Inositol—clinical applications for exogenous use." *Alternative MedRev*, 3:432-447 (1998).

Barkai AI, Dunner DL, Gross HA, Mayo P, Fieve RR. "Reduced myo-inositol levels in cerebrospinal fluid from patients with affective disorder." *Biol Psychiatry*, 13:65-72 (1978).

Levine J, Barak Y, Gonzalves M, Szor H, Elizur A, Kofman O, Belmaker RH. "Double-blind, controlled trial of inositol treatment of depression." *Am J Psychiatry*, 152:792-794 (1995).

Levine J, Barak Y, Kofman O, Belmaker RH. "Follow-up and relapse analysis of an inositol study of depression." *Isr J Psychiatry Relat Sci*, 32:14-21 (1995).

Benjamin J, Levine J, Fux M, Aviv A, Levy D, Belmaker RH. "Double-blind, placebo-controlled, crossover trial of inositol treatment for panic disorder." *Am J Psychiatry*, 152:1084-1086 (1995).

Ikemoto A, Kobayashi T, Emoto K, Umeda M, Watanabe S, Okuyama H. "Effects of docosahexaenoic and arachidonic acids on the synthesis and distribution of aminophospholipids during neuronal differentiation of PC 12 cells." *Arch Biochem Biophys*, 364:67-74 (1999).

Green P, Glozman S, Kamensky B, Yavin E. "Developmental changes in rat brain membrane lipids and fatty acids: The preferential prenatal accumulation of docosahexaenoic acid." *JLipidRes*, 40:960-966 (1999).

Stevens LJ, Zentall SS, Deck JL, Abate ML, Watkins BA, Lipp SR, Burgess JR. "Essential fatty acid metabolism in boys with attention-deficit hyperactivity disorder." *Am J Clin Nutr*, 62:761-768 (1995).

Stevens LJ, Zentall SS, Abate ML, Kuczek T, Burgess JR. "Omega-3 fatty acids in boys with behavior, learning, and health problems." *Physiol Behav*, 59:915-920 (1996).

Jones CR, Arai T, Rapoport SI. "Evidence for the involvement of docosahexaenoic acid in cholinergic stimulated signal transduction at the synapse." *Neurochem Res*, 22:663-670 (1997).

Itokazu N, Ikegaya Y, Nishikawa M, Matsuki N. "Bidirectional actions of docosahexaenoic acid on hippocampal neurotransmissions in vivo." *Brain Res*, 862:211-216 (2000).

Nishikawa M, Kimura S, Akaike N. "Facilitatory effect of docosahexaenoic acid on JV-methyl-D-aspartate response in pyramidal neurons of rat cerebral cortex." *J Physiol*, 475:83-93 (1994).

Poling JS, Vicini S, Rogawski MA, Salem N, Jr. "Docosahexaenoic acid block of neuronal voltage-gated K+ channels: Subunit selective antagonism by zinc." *Neuropharmacol*, 35:969-982 (1996).

Simopoulos A. "Omega-3 fatty acids in health and disease and in growth and development." *AmJ Clin Nutr* 191, 54:438-463. (1991).

Delion S, Chalon S, Guilloteau D, Lejeune B, Besnard J-C, Durand G. "Age-related changes in phospholipids fatty acid composition and monoaminergic neurotransmission in the hippocampus of rats fed a balanced or an n-3 poryunsaturated fatty acid-deficient diet." *JLipidRes*, 38:680-689 (1997).

Youdim KA, Martin A, Joseph JA. "Essential fatty acids and the brain: Possible health implications." *IntJDevl Neurosci*, 18:383-399 (2000).

Adams PB, Lawson S, Sanigorski A, Sinclair AJ. "Arachidonic to eicosapentaenoic acid ratio in blood correlates positively with clinical symptoms of depression." *Lipids*, 31 :S 167-S176 (1996).

Kalmijn S, Feskens EJM Launer LJ, Kromhout D. "Polyunsaturated fatty acids, antioxidants, and cognitive function in very old men." *Am J Epidemiol*, 145:33-41 (1997).

Newman PE. "Could diet be one of the causal factors of Alzheimer's disease?" *Med Hypotheses*, 39:123-126 (1992).

Okada M, Amamoto T, Tomonaga M, Kawachi A, Yazawa K, Mine K, Fujiwara M. "The chronic administration of docosahexaenoic acid reduces the spatial cognitive deficit following transient forebrain ischemia in rats." *Neurosci*, 71:17-25 (1996).

Shikano M, Masizawa Y, Yazawa K. "Effect of docosahexaenoic acid on the generation of platelet-activating factor by eosinophilic leukemia cells, Eol-1." *J Immunol*, 150:3525-3533 (1993).

Cornford EM, Braun LD, Oldendorf WH. "Carrier mediated blood-brain barrier transport of choline and certain choline analogs." *J Neurochem*, 30:299-308. (1978).
Zeisel SH, Da Costa K-A, Frankjin PD, Alexander EA, Lamont JT, Sheard NF, Beiser A. Choline, "An essential nutrient for humans." *FASEB J*, 5:2093-2098 (1991).
Wurtman RJ, Hirsch MJ, Growdon JH. "Lecithin consumption raises serum-free- choline levels." *Lancet*, 2M-69 (1977).
Blusztajn JK, Wurtman RJ. "Choline and cholinergic neurons." *Science*, 221:614:620 (1983).
Davis KL, Mohs RC, Tinklenberg JR, Hollister LE, Pfefferbaum A, Kopell BS. "Cholinomimetics and memory. The effect of choline chloride." *Arch Neurol*, 37:49-52 (1980).
Mohs RC, Davis KL, Tinklenberg JR, Hollister LE. "Choline chloride effects on memory in the elderly." *Neurobiol Aging*, 1:21-25 (1981).
Buchmn AL, Sohel M, Brown M, Jenden DJ, Ahn C, Roch M, Brawley TL. "Verbal and visual memory improve after choline supplementation in long-term total parenteral nutrition: A pilot study." *JP£TV*, 25:30-35 (2001).
Sitaram N, Weingartner H, Gillin JC. "Human serial learning: Enhancement with arecholine and choline and impairment with scopolamine." *Science*, 210:274-276 (1978).
Sitaram N, Weingartner H, Caine ED, Gillin JC. "Choline: Selective enhancement of serial learning and encoding of low imagery words in man." *Life Sci*, 22:1555-1560 (1978).
Su T-Z, Campbell GW, Oxender DL. "Glutamine transport in cerebellar granule cells in culture." *Brain Res*, 757:69-78 (1997).
Pow DV, Robinson SR. "Glutamate in some retinal neurons is derived solely from glia." *Neurosci*, 60:355-366 (1994).
Kapetanovic IM, Yonekawa WD, Kupperberg HJ. "Time-related loss of glutamine from hippocampal slices and concomitant changes in neurotransmitter amino acids." *JNeurochem*, 61:865-872 (1993).
Niihara Y, Zerez CR, Akiyama DS, Tanaka KR. "Oral L-glutamine therapy for sickle cell anemia: 1. Subjective clinical improvement and favorable change in red cell NAD redox potential." *Am JHematol*, 58:117-121 (1998).
Geller SJ. "Comparison of a tranquilizer and a psychic energizer." *JAMA*, 174:481-484 (1960).
Lewis JA, Young R. "Deanol and methylphenidate in minimal brain dysfunction." *Clin Pharmacol Ther*, 17:534-540 (1975).
ZS-Nagy I, Floyd RA. "Electron spin resonance spectroscopic demonstration of the hydroxyl free radical scavenger properties of dimethylaminoethanol in spin trapping experiments confirming the molecular basis for the biological effects of centrophenoxine." *Arch Gerontol Geriatr*, 3:297-310 (1984).
Oettinger L. "The use of Deanol in the treatment of disorders of behavior in children." *JPediatr*: 671-675, (1958).
Ferris SH, Sathananthan G, Gershon S, Clark C. "Senile dementia: Treatment with Deanol." *J Am Geriatr Soc*, 25:241-244 (1977).
Dimpfel W, Hofrnan HC, Prohaska A, Schober F, Schellenberg R. "Source density analysis of ftmctional topographical EEG: Monitoring of cognitive drug action." *Eur JMed Res*, 1:283-290 (1995-1996).
Ved HS, Koenig ML, Dave JR, Doctor BP. "Huperzine A, a potential therapeutic agent for dementia, reduces neuronal cell death caused by glutamate." *NeuroReport*, 8:963-968 (1997).
Cheng DH, Ren H, Tang X-C. "Huperaine A, a novel promising acetylcholinesterase inhibitor." *NeuroReport*, 8:97-101 (1996).
Hanin I, Tang X-C, Kindel GL, Kozikowski AP. "Natural and synthetic Huperzine A: Effect on cholinergic function in vitro and in vivo." *Annals NYAcad Sci* 695:304-306 (1993).
Tang X-C. "Huperzine A (Shuangyiping): promising drug for Alzheimer's research." *Ada Pharmacol Sinica*, 17:481-484 (1996).
Xiong ZQ, Han YF, Tang X-C. "Huperzine A ameliorates the spatial working memory impairments induced by AF64A." *NeuroReport*, 6:2221-2224 (1995).
Perry EK, Tomlinson BE, Blessed G, Bergmann K, Gibson PH, Perry RH. "Correlation of cholinergic abnormalities with senile plaques and mental test scores in senile dementia." *Br MedJ*, 2:1457-1459 (1978).

Wilcock GK, Esiri MM, Bowen DM, Smith CCT. "Alzheimer's disease. Correlation of cortical choline acetyltransferase activity with the severity of dementia and histological abnormalities." *JNeurolSci*, 57:407-417 (1982).
Thai LI, Masur DM, Blau AD, Fuld PA, Klauber MR. "Chronic oral physostigmine without lecithin improves memory in Alzheimer's disease." *J. Am GeriatrSoc*, 37:42-48 (1989).
Summers WK, Majovski LV, Marsh GM, Tachiki K, Kling A. "Oral tetrahydroaminoacridine in long-term treatment of senile dementia, Alzheimer type." *NewEnglJMed*, 315:1241-1245 (1986).
Xu S-S, Cai Z-Y, Qu Z-W, Yang R-M, Cai Y-L, Wang G-Q, Su X-Q, Zhong X-S, Cheng R-Y, Xu W-A, Li J-X, Feng B. "Huperzine-A in capsules and tablets for treating patients with Alzheimer's disease." *Ada Pharmacol Sinica*, 0:486-490 (1999).
Xu S-S, Gao Z-X, Weng Z, Du Z-M, Xu W-A, Yang J-S, Zhang M-L, Tong Z-H, Fang Y-S, Chai X-S, Li S-L. "Efficacy of tablet huperzine-A on memory, cognition, and behavior in Alzheimer's disease." *Ada Pharmacol Sinica*, 16:391-395 (1995).
Sun Q-Q, Xu S-S, Pan J-L, Guo H-M, Cao W-Q. "Huperzine-A capsules enhance memory and learning performance in 34 pairs of matched adolescent students." *Ada Pharmacol Sinica*, 20:601-603 (1999).
Drago F, Valerlo C, D'Agata V, Astuto C, Spadaro F, Continella G, Scapagnini U. "Pyroglutamic acid improves learning and memory capacities in old rats." *Functional Neurol*, 3:137-143 (1988).
Drago F, Continella G, Valerio C, D'Agata V, Astuto C, Spadaro F, Scapagnini U. "Effects of pyroglutamic acid on learning and memory processes of the rat." *Acta Therapeutica*, 13:587-594•(1987).
Spignoli G, Magnani M, Giovannini MG, Pepeu G. "Effect of pyroglutamic acid stereoisomers on ECS and scopolamine-induced memory disruption and brain acetylcholine levels in the rat." *Phamacol Res Commun*, 19:901-912 (1987).
Grioli S, Lomeo C, Quattropani MC, Spignoli G, Villardita C. "Pyroglutamic acid improves the age associated memory impairment." *Fundam Clin Pharmacol*, 4:169-173 (1990).
Singh HK, Dhawan BN. "Neuropsychopharmacological effects of the Ayurvedic nootropic *Bacopa monniera* Linn. (*Brahmi*)." *Indian J Pharmacol*, 29:S359:S365 (1997).
Morgan M, Bone K. "*Brahmi* (*Bacopa*)—revered Ayurvedic herb." *Modern Phytotherapist*, 5:21-27 (1999).
Singh HK, Dhawan BN. "Effect of *Bacopa monniera* Linn. {*Brahmi*) extract on avoidance responses in rat." *J Ethnopharmacol*, 5:205-214 (1982).
Singh HK, Rastogi RP, Srimal RC, Dhawan BN. "Effect of bacosides A and B on avoidance responses in rats." *Phytother Res*, 2:70-75 (1988).
Bhattacharya SK, Ghosal S. "Anxiolytic activity of a standardized extract of *Bacopa monniera*: An experimental study." *Phytomed*, 5:77-82 (1998).
Dar A, Channa S. "Calcium antagonistic activity of *Bacopa monniera* on vascular and intestinal smooth muscles of rabbit and guinea-pig." *J Ethnopharmacol*, 66:167-174 (1999).
Singh RH, Lallan S. "Studies on the anti-anxiety effect of the *Medhya rasayana* drug, *Brahmi* {*Bacopa monniera* Wettst.)—Part 1." *J Res Ayurveda Siddha*, 1-.133-148 (1980).
Ghosh S, Kar SK. "Clinical trial on *Brahmi*—Part II. Psychological investigation with normals." *J Exptl Med Sci*, 10:12-13 (1996).
Sharma R, Chaturvedi C, Tewari PV. "Efficacy of *Bacopa monnieri* in revitalizing intellectual functions in children." *J Res Indian Med*, 3:1-17 (1987).
Sharma, R., C. Chaturvedie and P.V. Tewari . "Management of Tropical Pulmonary Eosinophilia in Children with Ayurvedic Drugs," *J Res Indian Med* 1987; 3:1 -2.
Abhang R. "Study to evaluate the effect of a micro (*Suksma*) medicine derived from *Brahmi* (*Herpestris monierrd*) on students of average intelligence." *J Res Ayurvedia Siddha*, 14:10-24 (1993).
Martis G, Rao A, Karanth KS. "Neuropharmacological activity of *Herpestis monniera*." *Fitoterapia*, 63:3 99-404 (1992).
Sara SJ, Devauges V. "Priming stimulation of locus coeruleus facilitates memory retrieval in the rat." *Brain Res*, 438:299-303 (1988).
Denoblevj. "Vinpocetine enhances retrieval of a step-through passive avoidance response in rats." *Pharmacol Biochem Behavior*, 26:183-186 (1987).

Groo D, Palosi E, Szporny L. "Comparison of the effects of vinpocetine, vincamine, and nicergoline on the normal and hypoxia-damaged learning process in spontaneously hypertensive rats." *Drug Develop Res*, 15:75-85 (1988).

Bencsath P, Debreczeni L, Takacs L. "Effect of ethyl apovincaminate on cerebral circulation of dogs under normal conditions and in arterial hypoxia." *Arzneim- Forsch (Drug Res)*, 26:1920-1923 (1976).

Rischke R, Krieglstein J. "Protective effect of vinpocetine against brain damage caused by ischemia." *Japn J Pharmacol*, 56:349-356 (1991).

Sauer D, Rischke R, Beck T, Robberg C, Mennel H-D, Bielenberg GW, Krieglstein J. "Vinpocetine prevents ischemic cell damage in rat hippocampus." *Life Sci*,43:1733-1739 (1988).

Lakics V, Sebestyen MG, Erdo SL. "Vinpocetine is a highly potent neuroprotectant against vertridine-induced cell death in primary cultures of rat cerebral cortex." *NeurosciLett*, 185:127-130 (1995).

Nicholson CD. "Pharmacology of nootropics and metabolically active compounds in relation to their use in dementia." *Psychopharmacol*, 101:147-159 (1990).

Tretter L, Adam-Vizi V. "The neuroprotective drug vinpocetine prevents veratridine-induced [Na]\ and [Ca ], rise in synaptosomes." *NeuroReport*, 9:1849-1853 (1998).

Erdo SL, Cai N-S, Wolff Jr., Kiss B. "Vinpocetine protects against excitotoxic cell death in primary cultures of rat cerebral cortex." *Eur J Pharmacol*, 187:551-553 (1990).

Miyamoto M, Murphy TH, Schnaar RL, Coyle JT. "Antioxidants protect against glutamate-induced cytotoxicity in a neuronal cell line." *J Pharmacol Exptl Ther*, 250:1132-1140 (1989).

Ishihara K, Katsuki H, Sugimura M, Satoh M. "Idebenone and vinpocetine augment long-term potentiation in hippocampal slices in the guinea pig." *Neuropharmacol*, 28:569-573 (1989).

Coleston DM, Hindmarch I. "Possible memory-enhancing properties of vinpocetine." *Drug Develop Res*, 14:191-193 (1988).

Paulo T, Toth PT, Nguyen TT, Forgacs L, Torok TL, Magyar K. "HJNoradrenaline-releasing action of vinpocetine in the isolated main pulmonary artery of the rabbit." *J Pharm Pharmacol*, 38:668-673 (1986).

Karpati E, Szporny L. "General and cerebral haemodynamic activity of ethyl apovincaminate." *Arzneim-Forsch (Drug Res)*, 26:108-1912 (1976).

Imamoto T, Tanabe M, Shimamoto N, Kawazoe K, Hirata M. "Cerebral circulatory and cardiac effects of vinpocetine and its metabolite, apovincaminic acid, in anesthetized dogs." *Arzneim-Forsch (Drug Res)*, 34:161-169 (1984).

Hagiwara M, Endo T, Hidaka H. "Effects of vinpocetine on cyclic nucleotide metabolism in vascular smooth muscle." *Biochem Pharmacol*, 33:453-457(1984).

Hadjiev D, Yancheva S. "Rheoencephalographic and psychological studies with ethyl apovincaminate in cerebral vascular insufficiency." *Arzneim-Forsch (Drug Res)*, 26:1947-1950 (1976).

Shibota M, Kakihana M, Nagaoka A. "The effect of vinpocetine on the brain glucose uptake in mice." *Folia Pharmacol Japon*, 80:221-224 (1982).

Rosdy B, Balazs M, Szporny L. "Biochemical effect of ethyl apovincaminate." *Arzneim-Forsch (Drug Res)*, 26:1923-1926 (1976).

Pantano P, Baron J-C, Lebrun-Grandie P, Duquesnoy N, Bousser M-G, Comar D. "Regional cerebral blood flow and oxygen consumption in human aging." *Stroke* 15:635-641 (1984).

Miyazaki M. "The effect of a cerebral vasodilator, vinpocetine, on cerebral vascular resistance evaluated by the Doppler ultrasonic technique in patients with cerebrovascular diseases." *Angiology*, 46:53-58 (1995).

Otomo E, Atarashi J, Araki G, Ito E, Omae T, Kuzuya F, Nukada T, Ebi O. "Comparison of vinpocetine with ifenprodil tartrate and dihydroergotoxine mesylate treatment and results of long-term treatment with vinpocetine." *Curr Ther Res* 19%5,37:%1 1-821, (1985); 37:811-21.

Manconi E, Binaghi F, Pitzus F. "A double-blind clinical trial of vinpocetine in the treatment of cerebral insufficiency of vascular and degenerative origin." *Curr Ther Res*, 40:702709 (1986).

Balestreri R, Fontana L, Astengo F. "A double-blind placebo controlled evaluation of the safety and efficacy of vinpocetine in the treatment of patients with chronic vascular senile cerebral dysfunction." *J Am Geriatr Soc*, 35:425-430 (1987).

Hindmarch I, Fuchs H-H, Erzigkeit H. "Efficacy and tolerance of vinpocetine in ambulant patients suffering from mild to moderate organic psychosyndromes." *Internal Clin Psychopharmacol*, 6:31-43 (1991).

Subhan Z, Hindmarch I. "Psychopharmacological effects of vinpocetine in normal healthy volunteers." *Eur J Clin Pharmacol*, 28:567-571 (1985).

Rice-Evans CA, Miller NJ, Paganga G. "Structure-antioxidant activity relationships of flavonoids and phenolic acids." *Free Red Biol Med*, 20:933- 956 (1996).

Rigo A, Vianello F, Clementi G. "Contribution of proanthocyanidins to the peroxy radical scavenging capacity of some Italian red wines." *JAgric Food Chem*, 48:1996-2002 (2000).

Bagchi D, Garg A, Krohn RL, Bagchi DJ, Balmoori J, Stohs SJ. "Protective effects of grape seed proanthocyanidins and selected antioxidants against TPA- induced hepatic and brain lipid peroxidation and DNA fragmentation, and peritoneal macrophage activation in mice." *Gen Pharmacol*, 30:771-776 (1998).

Frei B, Kim MC, Ames BN. "Ubiquinol-10 is an effective lipid-soluble antioxidant at physiological concentrations." *Proc NatlAcad Sci*, 87:4879-4883 (1990).

Facino RM, Carini M, Aldini G, Bombardelli E, Morazzoni P, Morelli R. "Free radicals scavenging action and anti-enzyme activities of procyanidines from *Vitis vinifera*." *Arzneim-Forsch (Drug Res)*, 44:592-601 (1994).

Bagchi B, Garg A, Krohn RL, Bagchi M, Tran MX, Stohs SJ. "Oxygen free radical scavenging abilities of vitamins C and E, and a grape seed proanthocyanidin extract in vitro." *Res Commun Molecular Pathol Pharmacol*, 95:179-189 (1997).

Packer L, Rimbach G, Virgili F. "Antioxidant activity and biologic properties of a procyanidin-rich extract from pine (*Pinus maritimd*) bark, pycnogenol." *Free Rad Biol Med*, 27:704-724 (1999).

Liu FJ, Zhang YX, Lau BHS. "Pycnogenol enhances immune and haemopoietic functions in senescence-accelerated mice." *Cell Mol Life Sci*, 54:1168-1172 (1998).

Salah N, Miller NJ, Paganga G, Tijburg L, Bolwell GP, Rice-Evans C. "Polyphenolic flavonoids as scavengers of aqueous phase radicals and as chain-breaking antioxidants." *Arch Biochem Biophys*, 322:339-346 (1995).

Cossins E, Lee R, Packer L. "ESR studies of vitamin C regeneration, order of reactivity of natural source phytochemical preparations," *Biochem Mol Biol Intern*, 45:583-597 (1998).

Saija A, Scalese M, Lanza M, Marzullo D, Bonina F, Castelli F. "Flavonoids as antioxidant agents: Importance of their interaction with biomembranes". *Free Rad Biol Med*, 19:481-486 (1995).

Rong Y, Li L, Shah V, Lau BHS. "Pycnogenol protects vascular endothelial cells from r-butyl hydroperoxide induced oxidant injury." *Biotechnol Ther*, 5:117-126 (1994-1995).

Wei ZH, Peng QL, Lau BHS. "Pycnogenol enhances endothelial cell antioxidant defenses." *Redox Report*, 3:219-224 (1997).

Kim J, Chehade J, Pinnas JL, Mooradian AD. "Effect of select antioxidants on malondialdehyde modification of proteins." *Nutrition*, 16:1079-1081 (2000).

Ueda T, Ueda T, Armstrong D. "Preventive effect of natural and synthetic antioxidants on lipid peroxidation in the mammalian eye." *Ophthalmic Res*, 28:184-192 (1996).

Kobayashi MS, Han D, Packer L. "Antioxidants and herbal extracts protect HT-4 neuronal cells against glutamate-induced cytotoxicity." *Free Rad Res*, 32:115-124 (2000).

Coyle JT, Puttfarcken P. "Oxidative stress, glutamate, and neurodegenerative disorders." *Science*, 262:689-695 (1993).

Olney JW. "Brain lesions, obesity, and other disturbances in mice treated with monosodium glutmate." *Science*, 164:719-721 (1969).

Pereira CMF, Oliveira CR. "Glutamate toxicity ona PC 12 cell line involves glutathione (GSH) depletion and oxidative stress." *Free Rad Biol Med*, 23:637-647 (1997).

Fitzpatrick DF, Bing B, Rohdewald P. "Endothelium-dependent vascular effects of pycnogenol." *J Cardiovasc Pharmacol*, 32:509-515 (1998).

Schmidt HHHW, Walter U. "No at work" *Cell*, 78:919-925 (1994).

Fremont L, Belguendouz L, Delpal S. "Antioxidant activity of resveratrol and alcohol-free wine polyphenols related to LDL oxidation and polyunsaturated fatty acids." *Life Sci*, 64:2511-2521 (1999).
Chen CK, Pace-Asciak CR. "Vasorelaxing activity of resveratrol and quercetin in isolated rat aorta." *Gen Pharmacol*, 27:363-366 (1996).
Abalan F. "Primer in folic acid: Folates and neuropsychiatry." *Nutrition*, 15:595-598 (1999).
Alpert JE, Fava M. "Nutrition and depression: The role of folate." *NutrRev*, 55:145-149 (1997).
Abou-Saleh MT, Coppen A. "The biology of folate in depression: Implications for nutritional hypotheses of the psychoses." *J Psychiat Res*, 20:91-101 (1986).
Bottiglieri T, Laundy M, Crellin R, Toone BK, Carney MWP, Reynolds EH. "Homocysteine, folate, methylation, and monoamine metabolism in depression." *J Neurol Neurosurg Psychiatry*, 69:228-232 (2000).
Enzi G. "Folate status and cognitive impairment." *Aging Clin Exp Res*, 6:69-72 (1994).
Ortega RM, Manas LR, Andres P, Gaspar MJ, Agudo FR, Jimenez A, Pascual T. "Functional and psychic deterioration in elderly people may be aggravated by folate deficiency." *JNutr*,126:1992-1999 (1996).
Fava M, Borus JS, Alpert JE, Nierenberg AA, Rosenbaum JF, Bottiglieri T. "Folate, vitamin B12, and homocysteine in major depressive disorder." *Am J Psychiatry*, 154:426-428 (1997).
Levitt AJ, Joffe RT. "Folate, B12, and life course of depressive illness." *Biol Psychiatry*, 25:867-872 (1989).
Ghadirian AM, Ananth J, Engelsmann F. "Folic acid deficiency and depression." *Psychosomatics*, 21:926-929 (1980).
Prakash R, Petrie WM. "Psychiatric changes associated with an excess of folic acid." *Am J Psychiatry*, 139:1192-1193 (1982).
Clarke R, Smith AD, Jobst KA, Refsum H, Sutton L, Ueland PM. "Folate, vitamin B12, and serum total homocysteine levels in confirmed Alzheimer disease." *Arch Neurol*, 55:1449-1455 (1998).
Riggs KM, Spiro A, Tucker K, Rush D. "Relations of vitamin B-12, vitamin B-6, folate, and homocysteine to cognitive performance on the Normative Aging Study." *Am J Clin Nutr*, 63:306-314 (1996).
Snowdon DA, Tully CL, Smith CD, Riley KP, Markesbery WR. "Serum folate and the severity of atrophy of the neocortex in Alzheimer disease: Findings from the Nun study." *Am J Clin Nutr*, 1:993-998 (2000).
Carney M, Sheffield BF. "Associations of subnormal serum folate and vitamin B12 and effects of replacement therapy." *JNerv Merit Dis*, 150:404-412 (1970).
Levitt AJ, Wesson VA, Joffe RT. "Impact of suppression of thyroxine on folate status during acute antidepressant therapy." *Psychiatry Res*, 79:123-129 (1998).
Crayhon R. "The clinical applications of folk acid." *Jamer Neutraceutical Assoc*, 4:21-26 (2001).
Ubbink JB. "Should all elderly people receive folate supplements?" *Drugs Aging*, 13:415-420 (1998).
Kauwell GP, Lippert BL, Wilsky CE, Herrlinger-Garcia K, Hutson AD, Theriaque DW, Rampersaud GC, Cerda JJ, Bailey LB. "Folate status of elderly women following moderate folate depletion responds only to a higher folate intake." *JAfa/r*, 130:1584-1590 (2000).
Landgren F, Israelsson B, Lindgren A, Hultberg B, Andersson A, Brattstrom L. "Plasma homocysteine in acute myocardial infarction: Homocysteine-lowering effect of folic acid." *J Intern Med*, 237:381-388 (1995).
Kelly PJ, Rosand J, Plomaritoglou A, Chang Y, Kistler JP, Furie KL. "Mild-to-moderate hyperhomocyst(e)inemia and risk of stroke. Result of a meta-analysis." *Stroke*, 32:366 (2000).
Malinow MR, Nieto FJ, Szklo M, Chambless LE, Bond G. "Carotid artery intinalmedial wall thickening and plasma homocyst(e)ine in asymptomatic adults." *The Atherosclerosis Risk in Communities Study*. Circulation, 87:1107-1113 (1993).
Selhub J, Jacques PJ, Bostom AG, D'Agostino RB, Wilson PWF, Belanger AJ, O'Leary DH, Wolf PA, Rush D, Schaefer EJ, Rosenberg IH. "Relationship between plasma homocysteine, vitamin status and extracranial carotid artery stenosis in the Framingham study population." *JNutr*, 126:1258S-1265S (1996).

Pancharuniti N, Lewis CA, Sauberlich HE, Perkins LL, Go RCP, Alvarez JO, Macaluso M, Acton RT, Copeland RB, Cousins AL, Gore TB, Cornwell PE, Roseman JM. "Plasma homocyst(e)ine, folate, and vitamin B-12 concentrations and risk for early-onset coronary artery disease." *Am J Clin Nutr*, 59:940-948 (1994).
Stampfer MJ, Malinow R, Willett WC, Newcomer LM, Upson B, Ullmann D, Tishler PV, Hennekens CH. "A prospective study of plasma homocyst(e)ine and risk of myocardial infarction in US physicians." *JAMA*, 268:877-881 (1992).
Selhub J, Jacques PF, Bostom AG, D'Agostino RB, Wilson PWF, Belanger AJ, O'Leary DH, Wolf PA, Schaefer EJ, Rosenberg IH. "Association between plasma homocysteine concentrations and extracranial carotid-artery stenosis." *New Engl J Med*, 332:286-291 (1995).
Clarke R, Daly L, Robinson K, Naughten E, Cahalane S, Fowler B, Graham I. "Hyperhomocysteinernia: An independent risk factor for vascular disease." *New Engl J Med* \99\,32A:\U9-U55, (1981).
Boushey CJ, Beresford SAA, Omenn GS, Motulsky AG. "A quantitative assessment of plasma homocysteine as a risk factor for vascular disease. Probable benefits of increasing folic acid intakes." *JAMA*, 274:1049-1057 (1995).
Kang S-S, Wong PWK, Malinow MR. "Hyperhomocyst(e)mia as a risk factor for occlusive vascular disease." *Annu Rev Nutr*, 12:279-298 (1992).
Evers S, Kos HG, Grotenmeyer KH, et al. "Features, symptoms, and neurophysiological findings in stroke associate with hyperhomocysteinemia." *ArchNeurol*, 54:1276 (1997).
Perna AF, De Santo NG, Ingrosso D. "Adverse effects of hyperhomocysteinemia and their management by folic acid." *Miner Electrolyte Metab*, 23:174-178 (1997).
Harker LA, Ross R, Slichter SJ, Scott CR. "Homocysteine-induced arteriosclerosis. The role of endothelial cell injury and platelet response in its genesis." *JClin Invest*, 58:731-741 (1976).
Blann AD. "Endothelial cell damage and homocysteine." *Atherosclerosis*, 94:89-91 (1994).
La Rue A, Koehler KM, Wayne SJ, Chiulli SJ, Haaland KY, Garry PJ. "Nutritional status and cognitive functioning in a normally aging sample: a 6-yr reassessment." *Am JClin Nutr*, 65:20-29 (1997).
Lipton SA, Kim WK, Choi YD, Kumar S, D'Emilia DM, Rayudu PV, Arnelle DR, Stamler JS. "Neurotoxicity associated with dual actions of homocysteine at the N-methyl-D-aspartate receptor." *Proc Nat Acad Sci*, 94:5923-5928 (1997).
Beal MF, Swartz KJ, Finn SF, Mazurek MF, Kowall NW. "Neurochemical characterization of excitotoxin lesions in the cerebral cortex." *JNeurosci*, 11:147-158 (1991).
Ubbink JB, Van Der Merwe A, Vermaak WJH, Delport R. "Hyperhomocysteinemia and the response to vitamin supplementation." *Clin Invest*, 71:993-998 (1993).
Brouwer I A, Van Dusseldorp M, Thomas CMG, Duran M, Hautvast JGAJ, Eskes TKAB, Steegers-Theunissen RPM. "Low-dose folic acid supplementation decreases plasma homocysteine concentrations: a randomized trial". *Am J Clin Nutr*, 69:99-104 (1999).
Bunout D, Garrido A, Suazo M, Kauffinn R, Venegas P, De La Maza P, Petermann M, Hirsch S. "Effects of supplementation with folic acid and antioxidant vitamins on homocysteine levels and LDL oxidation in coronary patients." *Nutrition*, 16:107-110 (2000).
Clarke R, Armitage J. "Vitamin supplements and cardiovascular risk: Review of the randomized trials of homocysteine-lowering vitamin supplements." *Sem Thromb Hemostas* 2000, 26:341-348.
"Homocysteine Lowering Trialsists' Collaboration. Lowering blood homocysteine with folic acid based supplements: Meta-analysis of randomized trials." *Br MedJ*, 316:894-898 (1998).
Woo Ks, Chook P, Lolin YI, Sanderson JE, Metreweli C, Celermajer DS. "Folic acid improves arterial endothelial function in adults with hyperhomocysteinemia." *JAm Coll Cardiol*, 34:2002-2006 (1999).
Carney MWP, Toone BK, Reynolds EH. "S-Adenosylmethionine and affective disorder." *Am J Med*, 83(suppl 5A): 104-106 (1987).
Shane B. "Vitamin B12-Folate interrelationships." *Annu Rev Nutr*, 5:115-141 (1985).
Shevell MI, Rosenblatt DS. "The neurology of cobalamin." *Can JNeurol Sci*, 19:472-486 (1992).
Hector M, Burton Jr. "What are the psychiatric manifestations of vitamin B12 deficiency?" *JAm Geriatr Soc*, 36:1105-1112 (1987).

Mitsuyama Y, Kogoh H. "Serum and cerebrospinal fluid vitamin B12 levels in demented patients with CH3-B12 treatment—preliminary study." *Jpn JPsychiatr Neurol*, 42:65-71 (1988).

Lindenbaum J, Healton EB, Savage DG, Brust JCM, Garrett TJ, Podell ER, Marcell PD, Stabler SP, Allen RH. "Neuropsychiatric disorders caused by cobalamin deficiency in the absence of anemia or macrocytosis." *New EnglJ Med*, 318:1720-1728 (1988).

Bohnen N, Jolles J, Degenaar CP. "Lower blood levels of vitamin B12 are related to decreased performance of healthy subjects in the Stroop color-word test." *Neurosci Res Commun*, 11:53-56 (1992).

Goodwin JS, Goodwin JM, Garry PJ. "Association between nutritional status and cognitive functioning in a healthy elderly population." *JAMA*, 249:2917-2921 (1983).

Healton ED, Savage DG, Brust JCM, Garrett TJ, Lindenbaum J. "Neurologic aspects of cobalamin deficiency." *Medicine*, 70:229-245 (1991).

Carmel R. "Subtle and atypical cobalamin deficiency states." *AmJHematol*, 34:108-114 (1990).

Mittenberg W, Seidenberg M, O'Leary DS, Digiulio DV. "Changes in cerebral functioning associated with normal aging." *J Clin Exptl Neuropsychol*, 11:918-932 (1989).

Tetrud JW, Langston JW. "The effect of deprenyl (selegiline) on the natural history of Parkinson's disease." *Science*, 245:519-522 (1989).

American Medical Association. "Thiamin addition to alcohol." *Proceedings, 5(f Interim Meeting, American Medical Association*, (1996) p. 5.

Tucker DM, Penland JG, Sandstead HU, Milne DD, Heck DG, Klevay LM. "Nutrition status and brain function in aging." *Am J Clin Nutr*, 52:93-102 (1990).

Klimesch W, Schimke H, Ladurner G, Pfurtscheller G. "Alpha frequency and memory performance." *JPsychophysiol*, 4:381-390 (1990).

Lonsdale D, Shamberger RJ. "Red cell transketolase as an indicator of nutritional deficiency." *Am J Clin Nutr*, 33:205-211 (1980).

Benton D, Fordy J, Haller J. "The impact of long-term vitamin supplementation on cognitive functioning." *Psychopharmacol*, 117:298-305 (1995).

Benton D, Griffiths R, Haller J. "Thiamine supplementation mood and cognitive functioning." *Psychopharmacol*, 129:66-71 (1997).

Root EJ, Longnecker JB. "Brain cell alterations suggesting premature aging induced by dietary deficiency of vitamin B6 and/or copper." *Am J Clin Nutr*, 37:540-552 (1983).

Merrill AH, JR, Henderson JM. "Diseases associated with defects in vitamin B6 metabolism or utilization." *Annu Rev Nutr*, 7:137-156 (1987).

Dakshinamurti K, Leblancq WD, Herchl R, Havlicek V. "Nonparallel changes in brain monoamines of pyroxidine-deficient growing rats." *Exp Brain Res*, 26:355-366 (1976).

Siow YL, Dakshinamurti K. Effect of pyridoxine deficiency on aromatic L- amino acid decarboxylase in adult rat brain. *Exp Brain Res*, 59:575-581 (1985).

Stewart JW, Harrison W, Quitkin F, Baker H. "Low B6 levels in depressed outpatients." *Biol Psychiatry*, 19:613-616 (1984).

Carney MWP. "Vitamin deficiency and mental symptoms." *BrJPsychiat*, 156:878-882 (1990).

Kretsch MJ, Sauberlich HE, Newbrun E. "Electroencephalographic changes and periodontal status during short-term vitamin B-6 depletion of young, nonpregnant women." *Am J Clin Nutr*, 53:1266-1274 (1991).

Adams PW, Wynn V, Rose DP, Seed M, Folkard J, Strong R. "Effect of pyridoxine hydrochloride (vitamin B6) upon depression associated with oral contraception." *Lancet*, 1:897-904 (1973).

Hallert C, Astrom J, Walan A. "Reversal of psychopathology in adult celiac disease with the aid of pyridoxine (vitamin B6)." *Scand J Gastroenterol*, 18:299-304 (1983).

Deijen JD, Van Der Beek EJ, Orlebeke JF, Van Den Berg H. "Vitamin B-6 supplementation in elderly men: Effects on mood, memory, performance and mental effort." *Psychopharmacol* 1992, 109 AS9-496, (1992).

Buettnergr. "The pecking order of free radicals and antioxidants: Lipid peroxidation, -tocopherol and ascorbate." *Arch Biochem Biophys*, 300:535-543 (1993).

Schmidt R, Hayn M, Reinhart B, Roob G, Schmidt H, Schumacher M, Watzinger N, Launer LJ. "Plasma antioxidants and cognitive performance in middle-aged and older adults: Results of the Austrian Stroke Prevention Study." *J Am Geriatr Soc*, 46:1407-1410 (1998).

Beard JL, Connor JD, Jones BC. "Brain iron: Location and function." *Prog Food SciNutrSci\993,17:m-22\*, (1993); 17(3) : 183-221.

Kretsch MJ, Fong AKH, Green MW, Johnson HL. Cognitive function, iron status, and hemoglobin concentration in obese dieting women. *Eur J Clin Nutr* 1998,52:512-518.

Dallman PR. "Biochemical basis for the manifestations of iron deficiency." *Annu Rev Nutr*, 6:13-40 (1986).

Pollitt E. "Iron deficiency and cognitive function," *Annu Rev Nutr*, 13:521-537 (1993).

Dallman PR, Siimes MA, Stekel A. "Iron deficiency in infancy and childhood." *AmJClinNutr*, 33:86-118 (1980).

Pollitt E, Leibel RL. "Iron deficiency and behavior." *JPediatr*, 88:372-381 (1976).

Bruner AB, Jofife A, Duggan AK, Casella JF, Brandt J. "Randomized study of cognitive effects of iron supplementation in non-anemia iron-deficient adolescent girls." *Lancet*, 348:992-996 (1996).

Ballin A, Berar M, Rubinstein U, Kleter Y, Hershkovitz A. "Iron state in female adolescents." *AJDC*, 146:803-805 (1992).

Groner JA, Holtzman NA, Charney E, Mellits ED. "A randomized trial of oral iron on tests of short-term memory and attention span in young pregnant women." *JAdolesc Health Care*, 7:44-48 (1986).

Prasad AS. "Zinc: An overview." *Nutrition*, 11:93-99 (1995).

Toren P, Eldar S, Sela B-A, Wolmer L, Weitz R, Inbar D, Koren S, Reiss A, Weizman R, Laor N. "Zinc deficiency in attention-deficit hyperactivity disorder." *Biol Psychiatry*, 40:1308-1310 (1996).

Constantinidis J. "The hypothesis of zinc deficiency in the pathogenesis of neurofibrillary tangles." *Med Hypotheses*, 3 5:319-323 (1991).

Bekaroglu M, Asian Y, Gedik Y, Deger O, Mocan H, Erduran E, Karahan C. "Relationships between serum free fatty acids and zinc, and attention deficit hyperactivity disorder: A research note." *J Child Psychol Psychiat*, 37:225-227 (1996).

Penland JG. "Quantitative analysis of EEG effects following experimental marginal magnesium and boron deprivation." *Mag Res*, 8:341-358 (1995).

Mountokalakis TD. "Effects of aging, chronic disease, and multiple supplements on magnesium requirements." *Magnesium*, 6:5-11 (1987).

Frozel D, Coppen A, Marks V. "Plasma magnesium and calcium in depression." *BrJ Psychiat*, 115:1375-1377 (1969).

Nielsen FH. "The justification for providing dietary guidance for the nutritional intake of boron." *Biol Trace Element Res*, 66:319-330 (1998).

Hunt CD, Stoecker BJ. "Deliberations and evaluations of the approaches, endpoints and paradigms for boron, chromium and fluoride dietary recommendations." *JNutr*, 126:2441S-2451S (1996).

Penland JG. "Dietary boron, brain function, and cognitive performance." *Environ Health Perspect*, 102(suppl 7):65-72 (1994).

Tolman EL, Barris E, Burns M, Pansini A, Partridge R "Effects of vanadium on glucose metabolism in vitro." *Life Sci*, 25:1159-1164 (1979).

Shechter Y, Karlish SJD. "Insulin-like stimulation of glucose oxidation in rat adipocytes by vanadyl (IV) ions." *Nature*, 284:556-558 (1980).

Clausen T, Andersen TL, Stump-Johansen M, Petkova O. "The relationship between the transport of glucose and cations across cell membranes in isolated tissues. XI. The effect of vanadate on 45Ca-efflux and sugar transport in adipose tissue and skeletal muscle." *Biochimica Biophysica Ada*, 646:261-267 (1981).

Clark AS, Fagan JM, Mitch WE. "Selectivity of the insulin-like actions of vanadate on glucose and protein metabolism in skeletal muscle." *Biochem J*, 232:273-276 (1985).

Sekar N, Kanthasamy A, William S, Subramanaian S, Govindasamy S. "Insulinic actions of vanadate in diabetic rats." *Pharmacol Res*, 22:207-217 (1990).

Sakurai H, Tsuchiya K, Nukatsuka M, Softie M, Kawada J. "Insulin-like effect of vanadyl ion on streptozotocin-induced diabetic rats." *J Endocrinol*, 126:451-459 (1990).

Pandey SK, Anand-Srivastava MB, Srivastava AK. "Vanadyl sulfle-stimulated glucogen synthesis is associated with activation of phosphatidylinositol 3-kinase and is independent of insulin receptor tyrosine phosphorylation." *Biochemistry*, 37:7006-7014 (1998).

Cohen N, Halberstam M, Shlimovich P, Chang CJ, Shamoon H, Rosetti M. "Oral vanadyl sulfate improves hepatic and peripheral insulin sensitivity in patients with non-insulin-dependent diabetes mellitus." *J Clin Invest*, 95.2501-2509 (1995).

Castro J, Maquedano A, Olive M. "Lipid synthesis in isolated rat hepatocytes: Activation by insulin and vanadate and inhibition by ouabain." *Biochem Intern*, 9:413-420 (1984).

Rodriguez-Gil JE, Gomez-Foix AM, Fillat C, Bosch F, Guinovart JJ. "Activation by vanadate of glycolysis in hepatocytes from diabetic rats." *Diabetes*, 40:1355-1359 (1991).

Stanley BG, Kyrkouli SE, Lampert S, Leibowitz SF. "Neuropeptide Y chronically injected into the hypothalamus: A powerful neurochemical inducer of hyperphagia and obesity." *Peptides*, 7:1189-1192 (1986).

Morley JE, Levine AS, Gosnell BA, Kneip J, Grace M. "Effect of neuropeptide Y on ingestive behaviors in the rat." *Am JPhysiol*, 252:R599-R609 (1987).

Billington CJ, Briggs JE, Grace M, Levine AS. "Effects of intracerebroventricular injection of neuropeptide Y on energy metabolism." *Am JPhysiol*, 260:R321-R327 (1991).

Malabu UH, Dryden S, McCarthy HD, Kilpatrick A, Williams G. "Effects of chronic vanadate administration in the STZ-induced diabetic rat. The antihyperglycemic action of vanadate is attributable entirely to its suppression of feeding." *Diabetes*, 43:9-15 (1994).

Benton D, Cook R. "Selenium supplementation improves mood in a double-blind crossover trial." *Psychopharmacol*, 102:549-550 (1990).

Bendich A. "The potential for dietary supplements to reduce premenstrual syndrome (PMS) symptoms." *J Am Coll Nutr*, 19:3-12 (2000).

Thys-Jacobs S. "Micronutrients and the premenstrual syndrome: The case for calcium." *J Am Coll Nutr*, 1 9:220-227 (2000).

Thys-Jacobs S, Ceccarelli S, Biermana, Weisman H, Cohen M-A, Alvir J. "Calcium supplementation in premenstrual syndrome: A randomized crossover trial." *J Gen Intern Med*, 4:183-189 (1989).

Thys-Jacobs S, Starkey P, Bernstein D, Tian J. "Calcium carbonate and the premenstrual syndrome: Effects on premenstrual and menstrual symptoms." *Am J Obstet Gynecol*, 179:444-452 (1998).

Penland JG, Johnson PE. "Dietary calcium and manganese effects on menstrual cycle symptoms." *Am J Obstet Gynecol*, 168:1417-1423 (1993).

Facchinetti F, Borella P, Sances G, Fioroni L, Nappi R, Genazzani AR. "Oral magnesium successfully relieves premenstrual mood changes." *Obstet Gynecol*, 78:177-181 (1991).

Facchinetti F, Sances G, Borella P, Genazzani AR, Nappi G. "Magnesium prophylaxis pf menstrual migraine: Effects on intracellular magnesium." *Headache*, 31:298-301 (1991).

De Souza MC, Walker AF, Robinson PA, Bolland K. "A synergistic effect of a daily supplement for 1 month of 200 mg magnesium plus 50 mg vitamin B6 for the relief of anxiety-related premenstrual symptoms: A randomized, double- blind, crossover study." *J Women's Health & Gender-Based Med*, 9:131-139 (2000).

Benton D, Roberts G. "Effect of vitamin and mineral supplementation on intelligence of a sample of schoolchildren." *Lawcef*, 1:140-143 (1988).

Schoenthaller SJ, Bier ID. "Vitamin-mineral intake and intelligence: A macrolevel analysis of randomized controlled trials." *J Alternative Complementary Med*, 5:125-134 (1999).

\* cited by examiner

COMPOSITIONS FOR IMPROVING MENTAL PERFORMANCE

CROSS REFERENCE TO RELATED APPLICATIONS

This is a continuation of International Application No. PCT/US02/21062, with an International filing date of Jul. 3, 2002, which International Application claims the benefit of U.S. Provisional Application No. 60/302,653 filed on Jul. 5, 2001, both of which applications are hereby incorporated by reference in their entirety.

FIELD OF THE INVENTION

This invention pertains, in general, to the field of nutritional-dietary/herbal-botanical, neuro-support factors designed or intended for the sustenance of optimal healthy mental cognition. In particular, the present invention provides formulas for producing compositions for the structural/functional nutritional support for those who struggle with poor focus, concentration and/or memory. In addition, the present invention provides compositions comprising nutritional/botanical factors helpful to those who subjectively experience transient mental fatigue or poor cognitive function.

BACKGROUND OF THE INVENTION

All journal articles, other references, patents, and patent applications that are identified in this patent application are incorporated by reference in their entirety.

The role of nutrition and the positive influence of dietary-nutritional, herbal-botanical ingredients as they relate to optimal energy production, neurophysiology, and neurotransmitter synthesis/formation cannot be understated.

Physiology textbooks describe the brain as the most metabolically demanding of all organs (86). Representing only 2% of the total body weight, the brain consumes 50% of the circulating blood glucose, and over 20% of circulating oxygen. In essence, neurons have energy needs more than twice that of other cells. Since neural requirements for energy substantially exceed that of other cells in the body, Krebs-Cycle intermediates are metabolically essential ingredients for optimal ATP generation, optimal neural metabolism, and thus, improved mental acuity.

Also, neurotransmitters are naturally occurring molecules that act as biochemical messengers relaying nerve signals between neurons. Adequate production of the different types of neurotransmitters is responsible for proper mental functioning. Deficiencies of these neurotransmitters interfere with behavior, mood, concentration and memory.

Based on the brain's need for energy production and neurotransmitter synthesis, scientists postulate that the chemistry of our diet is a critical element in the subsequent triggering of neurotransmitter synthesis and efficient energy production, which jointly lead to normal/optimal cognitive function. Thus, a new class of research has evolved that investigates the effect of various dietary, nutritional and herbal constituents known to improve learning and memory. This class of "smart nutrients and foods" has been termed nootropics—meaning literally "toward the mind."

Exhaustive analytical investigation into nootropics has been ongoing, and several studies have confirmed the necessity of several key nutritional ingredients to mental health. In particular, researchers at the United States Department of Agriculture (USDA) mounted a study to examine how marginal nutritional deficiencies affect memory and mental function. They meticulously determined the nutritional status of twenty-eight healthy people age sixty and older, and then gave them challenging mental tasks to measure cognitive function. Significant relationships were noted between nutritional status and test performance. Subjects who had optimal levels of certain nutrients tested better than those with nutrient deficiencies. The nutrient groups' electrocardiogram (EEG) rating, which assesses activity in the brain, indicated superior brain functioning. This study suggested that even mild nutritional deficits might be responsible for cognitive decline and changes in brain function. The strongest associations were with thiamine (vitamin B1), riboflavin (vitamin B2), and iron. Beta-carotene, vitamin C, and zinc levels were also predictive of performance on mental function tests (1).

A much larger, long term study performed at the University of New Mexico School of Medicine followed 137 people between age sixty-six and ninety for six years. The participants in this study were educated, well nourished and had no memory problems. Their vitamin status was determined at the beginning of the study and again after six years. At the study's conclusion they were given tests determining cognitive function. Test performance was related to past and current nutritional status, and significant associations between mental function and vitamin status were noted. Those in the study group who had higher blood levels and intake of vitamins in the B-complex family (thiamin, riboflavin, niacin, and folate) performed better in tests of abstract thinking. High blood levels of vitamin C were associated with increased ability in performing visual and spatial tasks, and higher intakes of vitamin E, A, B6 and B12 correlated with better scores on both visual and spatial tasks, and higher intake of vitamins E, A, B6, and B12 correlated with better scores on visual and spatial recall and/or abstract thinking. The participants in this study who, on their own, had taken vitamin supplements, did better on difficult visual and spatial tests and on tests of abstract thinking (2).

In many children and teens, daily nutritional supplementation has shown to manifest profound cognitive benefits. For example, adding nutritional supplements to the diet has resulted in increased intelligence in children, even in the absence of malnutrition or poor cognitive function (24). In some cases, the benefits include the resolution of many of the symptoms associated with various learning disabilities, including attention deficit disorder (ADD), which is a term currently used to describe a condition that has had multiple labels in the past. Currently, more than ten prominent studies have shown that learning disabled/ADD children and adults suffering with similar symptomatology have special dietary needs for DHA (docosahexaenoic acid), thiamine, vitamin C, pyridoxine, calcium, magnesium, iron and zinc (27, 28, 29, 30, 31, 32, 33, 34, 35). In many of the previously referenced studies, when these nutrients are added to the diets of subjects suffering with learning disabilities/ADD, some symptoms are shown to significantly diminish, and in many cases resolve.

This invention provides unique formulas of nootropic nutrients and herbal extracts designed to provide specific dietary-nutritional and herbal-botanical support factors for cognitive function. Administration of the compositions based on these formula results in the efficient formation of mental energy and the synthesis of key neurotransmitters associated with memory, focus and concentration. The present formulas have increased bioavailability of constituent components and therefore have an enhanced synergistic affect on mental health.

The ingredients of the present invention are necessary constituents, co-factors and synergists in the formation and synthesis of the following energy substrates and neurotransmitters: acetylcholine, serotonin, dopamine, norepinephrine/epinephrine and adenosine triphosphate (ATP). All of these neurotransmitters and energy factors are intricately involved in mental cogmtion, neurological (as well as systemic) metabolism, the regulation of mood, and the ability to focus and concentrate, as well as learning, memory and numerous creative and analytical cognitive processes.

As a convenient addition to the daily diet, the formulas of the present invention provide a unique combination of energy precursors, neurological support antioxidants and nutrients, as well as many nootropic ingredients in their most bio available/absorbable forms to provide enhanced efficacy.

SUMMARY OF THE INVENTION

The present invention provides compositions formulated to provide support for mental performance and/or improve mental performance through the elimination of mental fatigue, as well as to improve memory, focus and concentration.

The present invention provides novel, comprehensive multi-vitamin/mineral formulas providing unique combinations of nutrient sources derived from "Krebs Cycle Intermediates." These sources of ingredients are more absorbable than ordinary sources of nutrients and thus, more likely to show an improvement in blood nutriture. In addition, these sources of nutrients provide precursors for ATP formation.

An unprecedented and quite notable feature is the fact that the present invention provides a unique combination of specific cognitive support factors. Although individually many of the nutrients have been clinically shown to enhance mental energy levels as well as support and enhance mental focus, concentration and memory, these nutrients have an enhanced synergistic affect when combined within the present composition.

The present invention constitutes novel, proprietary formulas designed to provide specific dietary-nutritional, and herbal-botanical support factors for cognitive function through the efficient formation of both mental energy, and the synthesis of key neurotransmitters associated with memory, focus, concentration and mood. The present also provides compositions and methods for the administration of the formulas of the present invention.

DETAILED DESCRIPTION OF THE INVENTION

I. General Description

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

The current inventions in this application are in the fields of nutritional supplements and methods of using such supplements to improve and maintain memory, focus, concentration and mood.

The Detailed Description and Examples provide detailed scientific results that can be used by a skilled artisan to prepare and administer the compositions of the present invention. The description of the present invention provided herein has been given for clearness and understanding only and no unnecessary limitations should be understood therefrom as modifications will be obvious to those skilled in the art.

II. Components of the Composition

The composition of this invention consists primarily of the following ingredients: B-complex vitamins, antioxidants, minerals, phosphatidyl serine (PS), choline, dimethyl-aminoethanol (DMAE), docosahexaenoic acid (DHA), L-pyroglutamic acid, as well as herbal extracts from *Bacopa monniera, Vinca minor* and *Huperzia serrata*. Each of these components is more clearly defined below.

A. B-Complex Vitamins

Among the most important nutrients known to be involved in maintaining optimal mental function are the B-complex vitamins. These nutrients play both direct and indirect roles in neurological function. The indirect role the B vitamins play in cognitive function are underscored by their involvement on methylation—the process by which toxic byproducts of cellular metabolism are removed from the body.

Methylation is the body's chief mechanism for detoxification. It is in essence, housecleaning on the cellular level. When this process goes awry, there is a buildup of highly toxic homocysteine (a byproduct of normal amino acid metabolism). Elevated homocysteine is shown to result in viscous blood (resulting in decreased neural and systemic oxygenation), increased free radical pathology, initiates and accelerates arteriosclerosis, cancer, neuro-vascular decline, neuro-degenerative disorders, and is a marker for memory loss, cognitive dysfunction and Alzheimer disease (3, 4, 5). The process of optimal methylation can be nutritionally supported, and toxic levels of homocysteine can be reduced and eliminated by the consumption of specific B-complex vitamins (3, 4, 5, 6). In addition, studies show that people with the highest blood nutriture of B-complex vitamins score highest on tests of cognitive function (3).

In addition, B-vitamins are known as nutritional cofactors that act as biochemical "spark plugs" in mitochondria, and therefore act to further nurture and support optimal neural metabolism. The present invention incorporates unique metabolically enhanced forms of B-vitamins. The B-vitamin complex is present in the inventive formulation at about 1% to about 10% of the overall composition. Constituents of the B-complex contemplated by the present invention are further described below.

Folic acid is a collective term for pteroylglutamic acids and their oligoglutamic acid conjugates. Supplemental folic acid is important for men, women and children of all ages. Mild deficiencies have been found to be associated with irritability, depression, poor cognitive function and memory loss (3, 4, 7, 8, 9). Deficiencies are quite common in the population (7, 8, 9). Folic acid may comprise about 400 micrograms ("mcg") of the overall composition. Preferably from about 100 mcg to about 1000 mcg, more preferably from about 200 mcg to about 800 mcg, and even more preferably from about 400 mcg to about 600 mcg. Vitamin B 1 (thiamin) was the first of the B vitamins to be discovered. It is required for the production of multiple enzymes that are necessary for the conversion of glucose into energy in the brain. This nutrient also mimics the activities of acetylcholine—the major learning neurotransmitter associated with attention, concentration and memory. Increased thiamin consumption is associated with improved cognitive function and faster reaction times, with participants subjectively describing supplementation effects as "feeling clearheaded, composed, and energetic" (1, 2, 4, 7, 10). Vitamin B1 may be present in the overall composition as thiamin, preferably from about 1 mg to about 25 mg, more preferably from about 2 mg to about 20 mg, and even more preferably from about 3 mg to about 10 mg.

It is also important to note that vitamin B5 (p antothenic acid) must be present for the synthesis of acetylcholine. The present herbal composition may contain Vitamin B5 as calcium pantothenate and/or pantethine, preferably as d-calcium pantothenate. Vitamin B5 may comprise preferably from about 10 mg to about 100 mg, more preferably from about 12 mg to about 25 mg and most preferably from about 12 to 16 mg.

Niacin (vitamin B3) is necessary for the production of energy. In neurological tissue, niacin is located both in nerve cell membranes, where it helps facilitate nerve impulse transmission, and inside neurons (brain cells), where it is involved in metabolism and oxygen supply. A number of studies indicate that supplementing this nutrient improves brain function. For example, participants were tested in a double blind study for effects on short- and long-term memory. Memory tests were performed, and repeated after six weeks and revealed 10 percent to 40-percent improvements in both short- and long-term memory, compared to the placebo group (11). Vitamin B3 may be present in the compositions of the present invention either as inositol hexanicotinate, niacinamide, nicotinic acid and/or nicotinate; preferably inositol hexanicotinate and niacinamide are present in the composition; and most preferably both are present in equal amounts in the composition. Preferably from about 10 mg to about 100 mg, more preferably from about 15 mg to about 50 mg, and even more preferably from about 20 mg to about 30 mg of vitamin B3 is used within the present composition.

Vitamin B6 (pyridoxine) is required in the production of the neurotransmitters—norepinephrine, serotonin and dopamine. It has been shown to enhance memory and cognitive function, and low levels of this nutrient correspond to poor scores on tests of cognitive function and premature neural aging (2, 3, 4, 12, 13). In addition, deficiencies are not uncommon in the population (2, 3, 4, 12, 13). The Vitamin B6 in the present compositions may be either a pyridoxine, pyridoxal or pyridoxamine; and preferably Vitamin B6 is present in the composition as pyridoxal-5 phosphate, pyrodoxine and/or 30 pyrodoxine alpha keto-glutarate. Preferably pyridoxal-5 phosphate and pyrodoxine alpha keto-glutarate are present in the composition, and most preferably, pyridoxal-5 phospate comprises 33% of the Vitamin B6 present in the composition and pyrodoxine alpha keto-glutarate comprises preferably from about 33% to about 90%, more preferably from about 40% to about 80%, and even more preferably from about 50% to about 70% of the vitamin B6 present in the composition. In general, Vitamin B-6 comprises preferably from about 5 mg to about 100 mg, more preferably from about 10 mg to about 50 mg, and even more preferably from about 12 mg to about 30 mg.

Cobalamin, or vitamin B-12, is essentially the neuro-nutrient. It is the most important of the B-vitamins for proper cognitive function. It plays multiple roles, in methylation, production of healthy blood, as well as production of healthy myelin in neurons. Deficiencies are common, and marginal deficiencies are shown to result in depression as well as cognitive decline in the elderly. Scientists conclude that as much as fifty percent of mental confusion, deterioration and cognitive decline in the elderly may be attributed to a lack of this nutrient (1, 2, 3, 4, 5, 6, 14, 15, 16, 17). Although Vitamin B12 is cyanocobalamin by chemical definition, any substituted cobalamin such as adenosylcobalamin, cobalamin, hydroxocobalamin, or methylcobalamin may be used. Preferably, the Vitamin B 12 used within the present invention is present as an ion exchange residue of cyanocobalaniinin or a substituted cobalamin. The ion exchange resin is preferred as a result of this form appearing to exhibit enhanced stability. Preferably from about 10 mcg to about 100 mcg, more preferably from about 12 mcg to about 50 mcg, and even more preferably from about 15 mcg to about 30 mg of Vitamin B 12 are present in the composition.

B. Antioxidants

Supplemental antioxidants are critical for optimal mental performance and are present in nutritional constituent and herbal composition preferably from about 10% to about 40%, more preferably from about 12% to about 30%, and even more preferably from about 15% to about 33%.

For example, in an Austrian study of 1,769 people from ages fifty to seventy five, researchers found that individuals with low blood levels of vitamin E performed more poorly on tests of cognitive function than those with high blood levels of the vitamin (18). The present compositions contain Vitamin E as -tocopherol as well as other isomers of tocopherol and/or tocotrienol. Preferably Vitamin E is present as a d- or dl-isomer of -tocopherol, -tocopheryl acid succinate, or -tocopheryl acetate; most preferably it is present in the composition as d-tocopheryl. Vitamin E is present in the composition preferably from about 15 IU to about 400 IU, more preferably from about 20 IU to about 200 IU, and even more preferably from about 30 IU to about 100 IU.

Like Vitamin E, Vitamin A is a fat-soluble antioxidant that plays numerous protectant and physiological roles in the brain. Beta-carotene, a carotenoid, is a precursor to Vitamin A formation, and is converted into Vitamin A as needed. New research suggests that this nutrient is involved in brain function throughout life. Vitamin A has been described by Dr. Ronald Evans of the Salk Institute for Biological Studies in La 10 Jolla, Calif., as "a type of molecular key that unlocks one of the most powerful functions of the human brain, learning" (19). Vitamin A, typically associated with retinol, carotene, especially beta carotene, and carotenoids, is also within the present invention. Preferably the present invention includes beta carotene and other naturally occurring carotenoids. Preferably from about 2000 IU to about 5000 IU, more preferably from about 2500 IU to about 4500 IU, and even more preferably from about 4000 IU to about 5000 IU of Vitamin A are present in the herbal compositions of the present invention.

Vitamin C plays multiple important roles in cognitive function. As a matter of fact, it is so important to neural tissue that concentrations of Vitamin C are fifteen times higher in the brain than elsewhere in the body. It is also involved in the production of several neurotransmitters, including acetylcholine, dopamine and norepinephrine. Administration of this nutrient has been shown to increase IQ points, and the use of vitamin C to treat memory disorders is currently being explored (1, 2, 4, 7, 18, 20). Vitamin C, ascorbic acid, is also present in the herbal composition. Preferably, Vitamin C is present as ascorbic acid, sodium ascorbate, ascorbyl palmitate, calcium ascorbate, potassium ascorbate and/or zinc ascorbate. Most preferably each of these is present in the composition in equal amounts. Vitamin C comprises preferably from about 200 mg to about 1000 mg, more preferably from about 225 mg to about 500 mg, and even more preferably from about 250 mg to about 400 mg.

Also, naturally occurring antioxidants such as oligomeric proanthocyanidins may also be present in the herbal compositions of the present invention. These proanthocyanidins are obtained from fruits, vegeatables, nuts, seeds, flowers, and barks of plants and have been reported to have a broad spectrum of biological, pharmacological and therapeutic activities against free radicals and oxidative stress (87). Proanthocyanidins derived from the seeds and leaves of grapes such as the *Vitis vinifera* variety are incorporated into the present composition. The increased bioavailability of these naturally occurring antioxidants increases the effectiveness of the present composition and therefore makes their incorporation into the composition preferable to that of other proanthocyanidins. Commercially available grape seed extracts such as Activin® produced by InterHealth Nutritionals, Inc. can be used in the present composition. The proanthocyanidins derived from the grape seed and leaves comprise preferably from about 5 mg to about 100 mg, more preferably from about 8 mg to about 50 mg, and even more preferably from about 12 mg to about 25 mg.

C. Minerals

Minerals are another category of underrated neuro-nutrients that play vital roles in mental function. Normal brain function is dependent on several key minerals that make up only 0.5 percent of the brain by weight. Whereas fatty acids like DHA provide much of the structural bulk of the brain (approximately 70%), minerals constitute a small fraction of its mass. The present composition is comprised preferably from about 10% to about 50%, more preferably from about 15% to about 30%, and even more preferably from about 20% to about 25%.

Zinc for example, is essential for neural function and also doubles as an antioxidant. Magnesium is a necessary cofactor in over three hundred enzymatic reactions, many of which are essential in the processes of generating neurotransmitters, energy and ATP. The literature shows that iron deficiency, which exists in a significant number of children with learning disabilities, may be a causative factor for much of the symptomatology associated with such poor cognitive function (25, 26). Several studies have suggested that supplementation with zinc, magnesium and iron among other minerals may provide cognitive protective effects, as well as improve memory, communication, and understanding (1, 21, 22, 23).

Calcium is a second messenger in neuronal membranes, which means it acts like a traffic signal for uptake and release of neurotransmitters. A "green light" from calcium permits the release of a neurotransmitter into the synaptic intersection. A "red light" halts its passage into the receiving neuron. Calcium also interacts with potassium and sodium to maintain proper levels of nerve-cell stimulation. This is how the balance between nerve cell activation and inactivation is achieved in the brain. In addition, calcium interacts with zinc in the regulation of the neurotransmitter histamine, and is dependent on DHA for all of its membrane functions. Thus calcium, in an elaborate concert with other neuro-nutrients regulates the speed, intensity, and clarity of every message that passes between brain cells.

Again, these underrated neuro-nutrients are crucial for healthy neurological function that ensures the activation of neuronal communication, regulation of neural metabolism, and protection of the brain against free-radical oxidation and toxic-metal contamination. Of all the minerals, calcium, magnesium, zinc and iron play the largest roles in brain function and constitute most of the mineral content in the brain.

In order to maximize neurotransmission and thus cognitive function, current research clearly supports the necessity of improving dietary intake of these nutrients. Quite paradoxically however, calcium, magnesium and zinc aggressively compete for uptake in the gastrointestinal tract, increasing the difficulty of introducing a clinically sufficient amount of each into the circulation (and brain) during one nutritionally supplemented meal. Thus, the quantity, and quality of the source of each nutrient becomes a key factor in developing an effective formula to improve nutriture and thus, mental cognition.

To overcome this common impediment to absorption, and thereby improve the effectiveness of the formulations of the present invention via bypassing the limiting factor of competitive inhibition, all minerals, including the critically important factors for cognitive function are provided in both optimal quantities and from multiple, highly absorbable, non-competitive sources called Krebs Cycle intermediates. These sources provide substantially greater absorption and neurological activity compared to other more commonly utilized mineral sources (36). Thus, the present composition provides preferably from about 25 mg to about 200 mg, more preferably from about 30 mg to about 100 mg, and even more preferably from about 40 mg to about 75 mg of calcium as calcium carbonate, chelated bisglycinate, calcium gluconate, calcium lactate, calcium phosphate, calcium citrate, calcium ascorbate, and/or calcium succinate. Likewise, preferably from about 50 mg to about 400 mg, more preferably from about 75 mg to about 300 mg, and even more preferably from about 100 mg to about 200 mg of magnesium is contained within the present inventive composition as magnesium oxide, magnesium gluconate, magnesium glycinate, chelated magnesium, magnesium citrate, magnesium malate, and/or magnesium taurinate. Preferably the composition contains magnesium citrate, magnesium malate, and magnesium taurinate. The composition also incorporates preferably from about 25 mg to about 99 mg, more preferably from about 35 mg to about 75 mg, and even more preferably from about 40 mg to about 60 mg of potassium as potassium citrate, potassium aspartate, and/or potassium ascorbate. Zinc may also be present in the composition bound to picolinate, citrate, acetate, gluconate, glycine, monomethionine, chelates and/or ascorbate form. Preferably the zinc is present bound to citrate and ascorbate and comprises preferably from about 5 mg to about 30 mg, more preferably from about 7 mg to about 25 mg, and even more preferably from about 10 mg to about 20 mg. Iron may comprise preferably from about 1 mg to about 18 mg, more preferably from about 2 mg to about 10 mg, and even more preferably from about 4 mg to about 8 mg. Typical iron compounds that my be present in the composition are ferrous fumorate, ferrous gluconate, ferrous sulfate, iron dextran, iron bisglycinate, and iron polysaccharide. Ferronyl® from Albion Labs provides a suitable commercial source for iron.

In addition, to further eliminate the possibility of competitive inhibition, multiple sources of each mineral component are present, preferably the composition includes about seven unique nutrient sources to deliver calcium and magnesium alone. Krebs Cycle intermediates are better absorbed, utilized and tolerated than the common inorganic or relatively insoluble mineral salts, including magnesium chloride, oxide, sulfate and carbonate (36, 37, 38, 39). As previously asserted, the Krebs Cycle intermediates have been carefully selected for the formulas of the present invention so as to play multiple roles in the generation of energy, and demonstrate a specific affinity for, and activity in the brain. The precise selection, multiple sources and ratios of these ingredients are intended to substantially increase the clinical effectiveness of the formulas of the present invention.

Additionally, minerals that are not directly linked to the nutritional well being of the brain also assist in its maintenance. For example, iodine is well known for its role in regulating the hormonal output of the thyroid. Since the hormones of the thyroid regulate metabolism and growth, an iodine deficiency has been demonstrated to adversely affect the mental capabilities of an individual in extreme cases leading to cretinism. The consumption of iodine has been directly linked to enhanced mental capabilities (88). The present invention incorporates preferably from about 5 mcg to about 100 mcg, more preferably from about 7 mcg to about 25 mcg, and even more preferably from about 10 mcg to about 20 mcg.

Preferably the iodine is derived from a natural source such as seafood, seaweed, or plants grown in iodine rich soil. Most preferably, the iodine is derived solely from kelp since it exhibits increased bioavailability.

Other minerals such as boron, chloride, copper, chromium, lithium, manganese, selenium, and vanadium may also be used within the present composition.

D. Phosphatidyl Serine (PS)

A supplement that enhances the cerebral cortex output of acetylcholine, phosphatidyl serine (PS) is the neurotransmitter associated with our ability to think, reason and concentrate. In addition, PS stimulates the synthesis and release of dopamine, related to heightened states of attention.

PS is the major phospholipid in the brain that plays a major role in determining the integrity and fluidity of cell membranes. PS supplementation in both animal studies and human clinical trials has been shown to significantly improve memory, mood and behavior, and to significantly eliminate depression. The most impressive PS studies have shown a marked improvement in cognitive function in the elderly. For example, supplementation with PS indicates that it may reverse up to twelve years of age-related mental decline (40). Furthermore, research demonstrates that PS supplementation results in a 15 percent improvement in learning ability and memory tasks (41). Human trials dating back to the 1970's support these findings. PS works by activating almost all regions of the brain, as seen in position emission tomography (PET) scans and EEGs (42, 43).

The present composition contains PS, preferably in the form of a lecithin phosphatidyl serine complex. While there is a bovine source of PS available, at this time the soy based raw material is the preferred raw material supplying PS. An example of a suitable commercially available source of PS would be Leci-PS® 30 P sold by Lucas Meyers. PS comprises preferably from about 2% to about 20%, more preferably from about 4% to about 10%, and even more preferably from about 5% to about 10%. Preferably from about 20 mg to about 200 mg, more preferably from about 30 mg to about 150 mg, and even more preferably from about 40 mg to about 100 mg of PS is used within the composition.

E. Choline/Phosphatidyl Choline

Classified by the National Academy of Sciences as an essential nutrient in 1998, choline falls into the general category of B-complex vitamins. It is a constituent of cell membranes and an essential precursor to the neurotransmitter acetylcholine—again, one of the brain's most important neurotransmitters associated with heightened states of attention, improved memory and learning.

Choline has demonstrated effects in humans including improvement in memory, thinking ability and serial-type learning in clinical studies (44). Dr. Christian Gillin, government scientist and top official at the National Institutes of Health, reports "[O]ur tests show that giving people choline increases their memory and learning ability by a startling 25 percent."

When combined with the B-complex and phosphatidyl serine, the raw materials are present for the formation of phosphatidyl choline—a facilitator of intercellular communication and an important component of nerve cell membranes.

The present composition contains preferably from about 10 mg to about 100 mg, more preferably from about 15 mg to about 75 mg, and even more preferably from about 20 mg to about 50 mg of choline, or about 1-3% of the overall composition. The choline is present in the composition as a bitartate, citrate, or chloride salt and phosphatidylcholine. Preferably choline is present in the composition as a choline bitartate.

F. Dimethyl-aminoethanol (DMAE)

DMAE is a natural substance present in foods such as anchovies and sardines (a reason fish is called brain food). It enhances memory and cognitive function by stimulating the production of choline, which, in turn, improves the synthesis of acetylcholine.

DMAE was commonly used prior to the 1980s and was especially effective in children with learning or behavioral problems associated with learning disabilities, shortened attention spans and/or hyperactivity (what we now define as ADD) (45, 46, 47, 48). Additional studies demonstrate improved mental concentration and sounder sleep in healthy subjects that consume DMAE (49).

In one study, 108 children with a learning disabilities behavior profile were given supplemental DMAE. Improvement was observed in the vast majority (71%) of the learning disabled/hyperactive children in the areas of increased attention span, decreased irritability, scholastic improvement, and, in some children, a rise in IQ (50).

In addition, DMAE is useful for adults with cognitive complaints. A 1996 German study examined the effects of DMAE along with vitamins and minerals on sixty men and women between the ages of forty and sixty-five who had difficulty concentrating during mental exercises. In this study, researchers obtained EEG recordings of volunteers before they began taking DMAE or placebo, and again after twelve weeks of supplementation. There were no changes in the brain waves in the subjects taking the placebo. In those taking DMAE, however, improvements were seen in the frontal and temporal lobes, areas of the brain that play an important role in attention, memory, concentration, and flexibility in thinking (51).

This ingredient was sold in the 1950's, 1960's and 1970's. It was marketed by a pharmaceutical company for its proven ability to accelerate mental processes, improve concentration span, and abolish early morning fogginess. It was considered to be more advantageous than amphetamines or stimulants in that it has no effect on heart rate or blood pressure, and DMAE does not induce jitteriness or anorexia (52, 53, 54, 55).

The present composition contains DMAE, preferably as a bitartrate. It may be present in the complex preferably from about 50 mg to about 600 mg, more preferably from about 100 mg to about 400 mg, and even more preferably from about 200 mg to about 300 mg., or about 5-25% of the overall complex.

G. Docosahexaenoic Acid (DHA)

The most abundant omega-3 fatty acid present in the brain is DHA. Research has shown DHA to play a critically important role in the integration and regulation of both the structure and neurological function of the brain.

Structurally, DHA is a long-chain polyunsaturated fatty acid with six double bonds, making it a hot bed of chemical and electrical activity. DHA is concentrated in the synaptic gaps between axons and dendrites, where neural communication takes place. It is also abundant in the neurons' mitochondria where ATP production takes place. In essence, where reasoning, learning and memory abound, there is an abundance of DHA.

Low levels of DHA are associated with a myriad of mental dysfunction including depression, aggression, memory loss, early dementia and Alzheimer's disease (56, 57). Interestingly, in many cases, depression, aggression and memory loss are shown to significantly improve, if not completely resolve, with the addition of this fatty acid to the diet. In addition, current research indicates that chronically low consumption of this fatty acid has been shown to be directly involved in some ADD/ADHD symptoms (28, 31, 32). For example, one study showed that a deficiency of DHA actually produced ADD/ADHD symptoms and demonstrated that children suffering with these symptoms had a marked reduction of DHA levels in the blood (28). Simply improving the blood level of this nutrient is shown to improve memory, visual acuity, and help maintain a positive mental state (28).

DHA is present in the composition. Preferably DHA concentrate fish oils 15% make up preferably from about 20 mg to about 200 mg, more preferably from about 30 mg to about 100 mg, and even more preferably from about 40 mg to about 60 mg of the composition, about 4% of the overall composition.

H. L-Pyroglutamic Acid

The amino acid L-Pyroglutamic acid helps maintain the sensitivity of receptor sites to acetylcholine at the post-synaptic gap between neurons. A given amount of acetylcholine will then have a larger, more pronounced effect, thereby enhancing neuroreceptor performance. Supplements of L-Pyroglutamic acid have been shown to enhance the ability to remember, focus and learn (58, 59).

In addition, L-Pyroglutamic acid is used as a building block for three related neurotransmitters: glutamic acid, 1-glutamine and gamma-amino buteric acid (GABA). GABA is an amino acid that is essential for brain metabolism, aiding in proper brain function. Together with niacinamide and inositol, it prevents anxiety and stress related messages from over-stimulating the motor centers of the brain, thus providing a focused, centered and calming effect.

The present invention contains preferably from about 25 mg to about 500 mg, more preferably from about 40 mg to about 250 mg, and even more preferably from about 50 mg to about 100 mg of L-Pyroglutamic acid, about 2-3% of the overall composition, and preferably contains about 10 mg of GABA, about 1% of the overall composition, as well.

I. Bacopa monniera (Bacosides)

*Bacopa monniera* is a traditional Ayurvedic herb utilized in India for more than 3,000 years to enhance memory capacity, improve intellectual and cognitive functions, reduce stress-induced anxiety and increase concentration.

*Bacopa monniera* has been shown to be a useful agent in reversing the symptoms of mental dysfunction in children (60) as well as a long history of research and use. The active ingredient in *Bacopa monniera* (called bacosides) is shown to regulate and restore proper synaptic activity in over-stimulated neurons, among other benefits.

Two active molecules with memory-enhancing properties were isolated from this plant and their chemical structures were determined; bacosides A and B (61).

Bacopa extracts have been shown to facilitate the acquisition, consolidation, retention and recall of learned tasks (62, 63). Research at Central Drug Research Institute (CDRI) showed that regular consumption of bacosides A and B extracted from the bacopa plant increases the protein kinase activity and new protein synthesis of the brain cells involved with learning and memory (64). The bacosides have also been shown to help repair damaged neurons by augmenting kinase, the protein involved in the synthesis of new neurons to replace old ones (64). As a result, depleted synaptic activity is restored leading to enhanced brain and memory function (65, 66).

Studies have shown that a student's concentration while studying is at its optimum during the first hour. However, in the second hour, concentration is reduced to 50 percent and by the third hour concentration is further reduced to 25 percent. Studies conducted by CDRI have conclusively shown that the concentration of students taking bacopa is maintained at optimum levels for three hours or more (62). Bacopa also increases mental retention. In normal circumstances, retention is 55 percent (i.e., 1 in 2 learned tasks are forgotten). However, after taking a standardized bacopa extract for a period of three months, the retention levels were shown to increase to 95 percent (i.e., only 1 in 20 learned tasks are forgotten)(62).

In 1993, Dr. Dubey and his team studied the effect of bacopa extracts in a placebo-controlled trial involving 232 children with mild to moderate mental deficiency. Significant improvement in both short-term and long-term memory was seen after daily therapy for one year, and significant improvement in memory was seen as early as three months following supplementation (67).

Bacopa extracts, preferably derived from the leaves of Baccopa monniera, are used within the present composition. Additionally, commercially available bacopa extracts such as Bacopin® manufactured by Sabinsa Corporation may be used. Bacopa extracts are present in the composition preferably from about 25 mg to about 200 mg, more preferably from about 40 mg to about 100 mg, and even more preferably from about 40 mg to about 80 mg.

J. Vinca minor (Vinpocetine)

Another effective plant-derived nootropic is vinpocetine. This herbal extract comes from the lesser periwinkle (Vinca minor). Vinpocetine has been shown to improve blood flow, circulation and oxygen utilization in the brain of animals and humans (68, 69, 70). It also protects neurons from the devastating effects of disrupted oxygen delivery. It is, therefore, a useful therapy for symptoms of senile dementia and cerebral vascular insufficiency (71, 72, 73, 74, 75).

Researchers at the University of Surrey in England administered either a high or low dose of vinpocetine or placebo to 203 patients with mild to moderate dementia. Significantly greater improvements were observed in cognitive performance and overall quality of life in the patients taking vinpocetine compared to the placebo group. Interestingly, there was little difference in the degree of improvement between those taking the high and low doses of the herb (76).

Vinpocetine also improves energy production in brain cells. It has been studied as a memory booster for young, healthy people, in whom it has been shown to improve short-term memory. In addition, it appears to have anticonvulsant properties. A Russian study of epileptic patients demonstrated that vinpocetine reduced the frequency and, in some cases, completely eliminated epileptic seizures in twenty of the thirty-one patients involved in the study. This nontoxic herbal extract was well tolerated in the bulk of participants in all of the clinical studies.

While many studies focus on the effects of vinpocetine for patients suffering from various degenerative conditions, researchers have also demonstrated positive effects in healthy individuals. In the United Kingdom, clinical trials in hundreds of individuals have shown that vinpocetine improves memory, including marked improvements in young and middle aged people (25-45 years of age)(77).

In a series of three double blind, placebo controlled crossover trials performed by the team of Dr. Hindmarch at the University of Leeds on healthy volunteers (aged 25-40), results demonstrated a significant memory improvement. The method of objective evaluation included the Steinberg Memory Test. These significant improvements clearly demonstrate the efficacy of Vinpocetine on young and healthy individuals (78).

The present composition contains preferably from about 1 mg to about 25 mg, more preferably from about 2 mg to about 20 mg, and even more preferably from about 4 mg to about 10 mg of Vinca minor. Commercially available sources of the extract, such as BioVinca™ distributed by Cyvex Nutrition, are suitable for use within the present composition.

K. *Huperzia serrata* (Huperzine A)

Huperzine A is an extract from club moss (*Huperzia serrata*) that has been used in Chinese medicine for centuries to treat inflammation and fever. In recent years, interest in this extract has shifted to its effects on the brain. Huperzine A boosts neurotransmission by naturally decreasing the hydrolysis of the neurotransmitter acetylcholine through inhibition of the enzyme acetylcholinesterase (79). In addition, huperzine protects neurons from damage and decreases neuronal cell death. It has been shown to enhance memory and improve cognitive function. Specifically, huperzine administration has been demonstrated to enhance focus, concentration and memory (80, 81). For patients with Alzheimer's disease and serious dementia, this herbal extract may have profound benefits (80, 84, 85).

In one study carried out in China, fifty patients with Alzheimer's disease were given 200 micrograms of huperzine A in four divided doses, and fifty-three other patients with similar degrees of dementia were administered a placebo. Fifty-eight percent of the people treated with the herb had improvements in memory, cognitive function and behavior, compared to thirty-six percent who improved on the placebo (83).

Interestingly, huperzine A appears to produce its cognitive improvements with fewer side effects, and its actions are of longer duration than current drugs which perform in much the same manner (82).

*Huperzia serrata* extracts, preferably derived from the Lycopodium serrata, are used within the present compositions preferably from about 25 mcg to about 200 mcg, more preferably from about 40 mcg to about 100 mcg, and even more preferably from about 50 mcg to about 75 mcg.

In addition to the primary components discussed above, the present herbal composition may also contain other nutrients or herbal extracts that assist, directly or indirectly, in maintaining or restoring mental health by improving the memory, focus, concentration or mood of a patient. Examples of other suitable constituents for the present compositions are vitamins such as Vitamin D3 (calciferol); amino acids such as L-Glutamine and N-acetyl-L-Tyrosine; and herbal extracts such as the anthocyanides derived from the fruit of *Vaccinium myrtillus* (Billberry). An example of the preferred formulation of the present composition and possible variants on the composition are provided below as Formulations I and II.

Formulation I

Formula I is provided in the following table:

TABLE 1

Formula I. Each 4 tablet serving contains the listed ingredients.

| Ingredient | Amount[1] |
|---|---|
| Vitamin A (natural beta carotene/mixed natural carotenoids) | 4000 IU |
| Vitamin D-3 (cholecalciferol) | 100 IU |
| Vitamin E (natural d-alpha succinate) | 30 IU |
| Vitamin B-1 (mononitrate) | 3 mg |
| Vitamin B-2 (riboflavin) | 2 mg |
| Vitamin B-3 (50% each inositol hexanicotinate & niacinamide) | 25 mg |
| Vitamin B-5 (d-calcium pantothenate) | 12 mg |
| Vitamin B-6 (33% pyridoxal-5-phosphate & 66% pryridoxine alpha keto glutarate) | 15 mg |
| Vitamin B-12 (cyanocobalmin as ion exchange resin) | 20 mcg |
| Folic Acid | 400 mcg |
| Biotin | 300 mcg |
| Vitamin C (16.67% each: ascorbic acid sodium ascorbate ascorbyl palmitate calcium ascorbate potassium ascorbate zinc ascorbate) | 250 mg |
| Calcium (33% each: citrate ascorbate succinate) | 50 mg |
| Magnesium (33% each: citrate malate taurinate) | 100 mg |
| Potassium (33% each: citrate aspartate ascorbate) | 50 mg |
| Iron (Ferronyl ® from Albion Labs) | 5 mg |
| Zinc (citrate Ascorbate) | 10 mg |
| Manganese (citrate) | 2 mg |
| Iodine (kelp) | 15 mcg |
| Copper (citrate Chelazome ® from Albion Labs) | 0.4 mg |
| Chromium (polynicotinate) | 100 mcg |
| Selenium (selenomethionine) | 20 mcg |
| Molybdenum (amino acid chelate) | 10 mcg |
| DHA Concentrate (15% fish oil) | 40 mg |
| Phosphatidyl Serine (soy lecithin) | 44 mg |
| Bilberry (standardized extract 25%) | 10 mg |
| Activin ® (grape seed and grape skin extract) | 10 mg |
| N-Acetyl-L-Tyrosine | 10 mg |
| Inositol | 25 mg |
| L-Pyroglutamic Acid | 50 mg |
| L-Glutamine | 105 mg |
| DMAE (bitartrate) | 271 mg |
| PAK (pyridoxal-alpha ketoglutarate) | 25 mg |
| Bacopa/Bacopin ® | 50 mg |
| GABA | 10 mg |
| Choline (bitartrate) | 25 mg |
| Vinpocitine | 5 mg |
| Huperzine Extract | 50 mcg |
| Boron (citrate) | 20 mg |
| Vanadium (vanadyl sulfate) | 5 mcg |
| Trace-Lyte ® (electrolyte concentrate from ___) | 2 mg |

[1]IU = international units; mg = milligram; mcg = microgram.

Formulation II.

Formula II is the same as Formula I except that instead of 20 mcg (i.e., micrograms) of selenium per 4 tablets there is 50 mcg of selenium per 4 tablets.

The exact proportions of the above-disclosed components may vary depending upon the concentration of active ingredients within the herbal compositions and the desire to optimize the bioavalability of these constituents of the composition. Using the guidance provided above and a basic knowledge of drug preparation and pharmacology, one skilled in the art could easily adjust the proportions of the separate components of the composition so as to obtain a composition which has the therapeutic affects discussed above and shown in the examples herein. The discussion of the proportions of ingredients in the composition provided above is merely meant as an example and is not intended to limit the scope of the present invention from including any novel combination of the disclosed herbal and non-herbal components which have the intended effect of relieving the symptoms of pain, fever and inflammation, as discussed herein.

III. Preparation of the Compositions

The compositions of this invention can be used in the form of a dietary supplement, for example, in solid, semi-solid or liquid form which contains the ingredients of the present invention in admixture with an organic or inorganic carrier or excipient suitable for external, enteral or parenteral applications.

The ingredients may be compounded, for example, with the usual non-toxic pharmaceutically acceptable carriers for tablets, pellets, capsules, suppositories, solutions, emulsions, suspensions, and any other form suitable for use. Formulations of the present invention encompass those which include various combinations of the exemplified ingredients, as well as carriers such as water, talc, glucose, lactose, gum acacia, gelatin, mannitol, starch paste, magnesium trisilicate, corn starch, keratin, colloidal silica, potato starch, urea and other carriers suitable for use in manufacturing preparations, in solid, semisolid or liquid form. In addition, auxiliary, stabilizing, thickening and coloring agents and perfumes may be added as desired.

For preparing solid compositions such as tablets or capsules, the principal ingredients are mixed with a carrier (e.g., conventional tableting ingredients such as corn starch, lactose, sucrose, sorbitol, talc, stearic acid, magnesium stearate, dicalcium phosphate or gums) and other diluents (e.g., water) to form a solid preformulation composition containing a substantially homogeneous mixture of a compositions of the present invention, or a non-toxic salt thereof. When referring to the preformulation compositions as substantially homogenous, it is meant that the active ingredients are dispersed evenly throughout the compositions so that the compositions may be readily subdivided into equally effective unit dosage forms such as tablets, pills and capsules. These solid preformulation compositions are then subdivided into unit dosage forms of the type described above containing predetermined amounts of the compositions of the present invention, preferably in tablets or pills. Generally, a person ingests 1 to 8 pills per day of the compositions provided by this invention. More preferably, a person ingests 4 or 8 pills per day of the compositions provided by this invention. Most preferably a person ingests 4 pills either once or twice a day to derive the benefits of the compositions provided by this invention.

The tablets or pills of the novel compositions can be coated or otherwise compounded to provide a dosage form affording the advantage of prolonged action. For example, the tablets or pills can comprise both an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms, in which the novel compositions of the present invention may be incorporated for administration orally or by injection, include aqueous solutions, suitably flavored syrups, aqueous or oil suspensions, and flavored emulsions with edible oils such as cottonseed oil, sesame oil, coconut oil, or peanut oil as well as elixirs and similar administration vehicles. Suitable dispersing or suspending agents for aqueous suspensions include synthetic natural gums, such as tragacanth, acacia, alginate, dextran, sodium carboxymethyl cellulose, methylcellulose, polyvinylpyrrolidone or gelatin.

Liquid preparations for oral administration may take the form of, for example, solutions, syrups or suspensions, or they may be presented as a dry product for reconstitution with water or other suitable vehicles before use. Such liquid preparations may be prepared by conventional means with additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); preservatives (e.g., methyl or propyl p-hydroxybenzoates or sorbic acid); and artificial or natural colors and/or sweeteners.

The ingredients may be formulated for parenteral administration by injection, which includes using conventional catheterization techniques or infusion. Formulations for injection may be presented in unit dosage form, e.g., in ampules, or in multi-dose containers, with an added preservative. The compositions may take such forms as suspensions, solutions or emulsions in oily or aqueous vehicles, and may contain formulating agents such as suspending, stabilizing, and/or dispersing agents. Alternatively, the active ingredients may be in powder form for reconstitution with a suitable vehicle, e.g., sterile pyrogen-free water, before use.

IV. Use of the Compositions

Another aspect of the invention relates to a method of improving mental performance comprising administering a composition comprising vitamin B12 on ion exchange resin, phosphatidyl serine (PS), DMAE, DHA, L-pyroglutamic acid, and herbal extracts from *Bacopa monniera*. In one embodiment, the composition is applied once a day. In another embodiment, the composition is applied twice a day.

In another embodiment, the method comprises administering in a daily dosage of one serving (4 tablets) of a composition comprising the ingredients of formula I or formula II. In another embodiment, the composition comprising the ingredients of formula I or formula II is applied in a daily dosage of two serving (4 tablets).

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES

1. Tucker, D M., et al. "Nutrition status and brain function in aging." *American Journal of Clinical Nutrition*, 52 (1): 93-102, July 1990.
2. La Rue, A., et al. "Nutritional Status and cognitive functioning in a normally aging sample: a 6-year reassessment." *American Journal of Clinical Nutrition*, 65 (1): 20-29, January 1997.
3. Riggs, K M., et al. "Relations of vitamin B-12, vitamin B-6, folate, and homocysteine to cognitive performance in the Normative Aging Study." *American Journal of Clinical Nutrition*, 63 (3): 306-314, March 1996.
4. Rosenberg, I H., and J W Miller. "Nutritional factors in physical and cognitive functions of elderly people."*American Journal of Clinical Nutrition*, 55 (6 Supplement): 1237-1243, June 1992.
5. Clarke, R., et al. "Folate, vitamin B12, and serum total homocysteine levels in confirmed Alzheimer disease." *Archives of Neurology*, 55 (4): 319-323, August 1991.
6. Graham, I M., et al. "Plasma homocysteine as a risk factor for vascular disease." The European Concerted Action Project. *Journal of the American Medical Association*, 277 (22): 1775-1781, Jun. 11, 1997.
7. Benton, D., et al. "The impact of long-term vitamin supplementation on cognitive functioning." *Psychopharmacology (Berlin)*, 111 (3): 298-305, February 1995.
8. Ghadirian, A M., et al. "Folic acid deficiency and depression."*Psychosomatics*, 21 (11): 926-929, November 1980.
9. Howard, J S., "Folate Deficiency in psychiatric practice." *Psychosomatics*, 16: 112-115, July/August/September 1975.
10. Benton, D., et al. "Thiamine supplementation, mood and cognitive functioning." *Psychopharmacology (Berlin)*, 129 (1): 66-71, January 1997.
11. Loriaux, S M., et al. "The effects of nicotinic acid and xanthinol nicotinate on human memory in different categories of age. A double blind study." *Psychopharmacology (Berlin)*, 87 (4): 390-395, 1985.
12. Jonathan S., et al. "Low B6 levels in depressed outpatients." *Biological Psychiatry*, 19 (4): 613-617, 1984.
13. Root, E J., and Longenecker, J B., "Brain cell alterations suggesting premature aging induced by dietary deficiency of vitamin B6 and/or copper." *The American Journal of Clinical Nutrition*, 37: 540-552, April 1983.
14. Healton, E B., et al. "Neurologic status of cobalamin deficiency." *Medicine*, (Baltimore) 70 (4): 229-245, July 1991.
15. Shevell, M I., and Rosenblatt, D S., "The neurology of cobalamin." *Canadian Journal of Neurologic Science*, 19 (4): 472-486, November 1992.
16. Hector, M., and Burton, J R., "What are the psychiatric manifestations of vitamin B 12 deficiency?" *The American Geriatrics Society*, 36 (12): 1105-1112, December, 1988.
17. Geagea, K., and Ananth, J., "Response of a psychiatric patient to vitamin B12 therapy." *Diseases of the Nervous System*, 343-344 June, 1975.
18. Schmidt, R., et al. "Plasma antioxidants and cognitive performance in middle-aged and older adults: results of the Austrian Stroke Prevention Study." *Journal of the American Geriatric Society*, 46 (11): 1407-1410, November 1998.
19. Chiang, M Y., et al. "An essential role for retinoid receptors RAR-beta and RXR-gamma in long-term potentiation and depression." *Neuron*, 21 (6): 1353-1361, December 1998.
20. Milner, G., "Ascorbic acid in chronic psychiatric patients—a controlled trial." *British Journal of Psychiatry*, 109: 294-299, March, 1963.
21. Constantinidis, J., "The hypothesis of zinc deficiency in the pathogenesis of neurofibrillary tangles." *Medical Hypotheses*, 35 (4): 319-323, August 1991.
22. Mountokalakis, T D., "Effects of aging, chronic disease, and multiple supplements on magnesium requirements." *Magnesium*, 6: 5-11, 1987.
23. Frizel, D., et al. "Plasma magnesium and calcium in depression." *British Journal of Psychiatry*, 115:1375-1377, 1969.
24. Benton, D., and Roberts, G., "Effects of vitamin and mineral supplementation on a sample of schoolchildren." *Lancet*, 1: 140-143, 1988.
25. Pollitt, E., and Leibel, R L., "Iron deficiency and behavior." *The Journal of Pediatrics*, 88 (3): 372-381, March, 1996.
26. Dallman P R., et al. "Iron deficiency in infancy and childhood." *The American Journal of Clinical Nutrition*, 33: 86-118, January, 1980.
27. Starobrat-Hermelin B, and Kozilec T. "The effects of magnesium physiological supplementation on hyperactivity in children with Attention Deficit Hyperactivity Disorder (ADHD). Positive response to magnesium oral loading test." *Magnesium Research*, 1997; 10(2): 149-156.
28. Steves L J, Zentall S S, Deck J L, Abate M L, Watkins B A, Lipp S R, and Burgess J R. "Essential Fatty acid metabolism in boys with Attention Deficit Hyperactivity Disorder." *American Journal of Clinical Nutrition*, 1995; 62: 761-768.
29. Toren P, Eldar S, Sela B A, Wolmer L, Weitz R, Inbar D, Koren S, Reiss A, Weizman R, and Loar N. "Zinc deficiency in Attention Deficit Hyperactivity Disorder." *Biological Psychiatry*, 1996; 40: 1308-1310.
30. Arnold E, Votolato N, Kleykamp D, Baker G, and Bornstein R. "Does hair zinc predict amphetamine improvement of ADD/Hyperactivity?" *Intern. J. Neuroscience*, 1990; 50:103-107.
31. Bekaroglu M, Asian Y, Gedik Y, Deger O, Mocan H, Erduran E, and Karahan C. "Relationships between serum free fatty acids and zinc, and Attention Deficit Hyperactivity Disorder: A research note." *J. Child Psychol. Psychiat*, 1996; 2: 225-227.
32. Stevens, L. et al. "Omega-3 fatty acids in boys with behavior, learning, and health problems." *Physiological Behavior*, 59(4-5): 915-20.
33. Sandyk R., "Zinc deficiency in attention deficit disorder—letter to the editor." *International Journal of Neuroscience*, 52:239-41, 1990.
34. Brenner, A., "The effects of megadoses of selected b-complex vitamins on children with hyperkinesis: controlled studies with long-term follow-up." *Journal of Learning Disabilities*, 15 (5): 258-264 May, 1982.
35. Carlton R M., et al. "Rational dosages of nutrients have a prolonged effect on learning disabilities." *Alternative Therapies*, 6 (3): 85-91, May, 2000.
36. Lindberg J S, et al. "Magnesium bioavailability from magnesium citrate and magnesium oxide." *J. Am. Coll. Nutr.* 1990; 9, 48-55.
37. Nicar M J, Pak C Y C. "Calcium bioavailability from calcium carbonate and calcium citrate." *J. Clin. Endocrinol. Metab.* 61: 391-393, 1985.
38. Harvey J A, Zobitz M A, Pac C Y C: "Calcium citrate: reduced propensity for the crystallization of calcium 38. oxalate in urine resulting from induced hypercalciuria of calcium supplementation" *J. Clin. Endocrinol. Metab.* 61:1223-1225, 1985.
39. Nicar M J, Pak C Y C: "Oral magnesium load test for the assessment of intestinal magnesium absorption: application in control subjects, absorptive hypercalciuria, primary hyperparathyroidism and hypoparathyroidism." *Min Elect Metab* 8:44-51, 1982.
40. Crook T H., et al. "Effects of phosphatidyl serine in age-associated memory imparement." *Neurology* 41: 644-649, 1991.
41. Crook, Thomas. 1998. *The Memory Cure*. New York: Pocket Books.
42. Soderberg, M., et al. "Fatty acid composition of brain phospholipids in aging and alzheimers disease." *Lipids,* 26(6): 421-425, June 1991.
43. Kidd P. "Phosphatidylserine: membrane nutrient for memory: a clinical and mechanistic assessment" *Altern. Med. Rev.* 1996; 1(2); 70-84.
44. Ladd S L., Sommer S A., LaBerge S., Toscano W: "Effect of phosphatidylcholine on explicit memory." *Clinical Neuropharmacology*, Vol. 16, No. 6, pp-540-549, 1993.
45. Oettinger L, "The use of Deanol in the treatment of disorders of behavior in children." *Journal of Pediatrics*, July-December 1958; 53: 671-675.
46. Lewis J A, Young R, "Deanol and methylphenidate in minimal brain dysfunction." *Clinical Pharmacology and Therapeutics,* 1975; 17(5): 534-540.
47. Coleman, N., et al. "Deanol in the treatment of hyperkenetic children." *Psychosomatics* (17): 68-72; April-June 1976.
48. Murphree, Jr., H B, Pfeiffer C C, Backerman I A, "The stimulant effect of 2-dimethylaminoethanol (Deanol) in human volunteer subjects." *Clinical Pharmacology and Therapeutics,* 1960; 1(3): 303-310.
49. Lemere F, Lasater J, "Deanol, a new cerebral stimulant for the treatment of neurasthenia and mild depression: A preliminary report." *American Journal of Psychiatry,* 1958; 144: 655-656.
50. Pfeiffer, C, et al. "Quantitative Comparisons of the electroencephalographic stimulant effects of deanol, choline and amphetamine." *Clinical Pharmacology and Therapeutics,* 1963; Volume 4 (4): 461-466.
51. Dimpfel, W., et al. "Source density analysis of functional topographical EEG: monitoring of cognitive drug action." *European Journal of Medical Research,* 1(6): 283-290, Mar. 19, 1996.
52. *The Merck Index, An Encyclopedia of Chemicals, Drugs, and Botanicals, Twelfth Edition* (2900) Therapeutic use: CNS Stimulant. Multiple, well established structural and functional references with long history of safe use.
53. Pfeiffer, C. "Stimulant effect of 2-Dimemylaminoethanol: Possible precursor to brain acetylcholine." *Science,* 126: 610-611, 1957.
54. Sergio, W., "Use of DMAE (2-Dimethylaminoethanol) in the induction of lucid dreams." *Medical Hypotheses,* 26, 255-257, 1988.
55. Stenback, F. et al. "Effect of lifetime administration of dimethylaminoethanol on longevity, aging changes, and cryptic neoplasms in C3H mice." *Mechanisms of Aging and Development,* 42:129-138, 1988.
56. Hibbeln J, Norman S, "Dietary Polyunsaturated fatty acids and depression: When cholesterol does not satisfy." *American Journal of Clinical Nutrition,* 62:1-9, 1995.
57. Schaefer E, "Decreased plasma phosphatidylcholine docosahexaenoic acid content in dementia," Presentation at: *Keeping your brain in shape*—New Insights Into DHA, New York City, Apr. 3, 1997.
58. Grioli S, et al. *Fundamentals of Clinical Pharmacology,* 4: 169-173, 1990.
59. Spignoli G, et al. *Pharmacological Research Communications,* 19 (12): 901-912.
60. Sharms R, Chaturvedi C, Tewari P V, "Efficacy of bacopa monnieri in revitalizing intellectual functions in children." *Journal Res. Edu. Ind,* January-June 1987: 1-12.
61. Chatterji N, Rastogi R, and Dhar M, "Chemical examination of *Bacopa monniera* Wettst: Part 1 isolation of chemical constituents." *Central Drug Institute, Lucknow, India:* 212-215, 1962.
62. Abhang R, "Study to evaluate a micro (Suksma) medicine derived from Brahmi on students of average intelligence." *J. Res. Ayurveda and Sidda,* 14:10-24, 1993.
63. Lodha R, and Bagga A, "Traditional Indian Systems of Medicine," *Annals of the Academy of Medicine,* Singapore, 1: 37-41, 2000.
64. Mahato S B, Gari S, and Chakravarty A K, "Bacopasaponins E and F: Two Jujubogenin bisdesmosides from *Bacopa monniera," Phytochemistry,* 53: 711-714, 2000.
65. Dhawan B N, and Singh H K, "Neuropsychopharmacological effects of the Ayurvedic Nootropic *Bacopa monniera* Linn. (Brahami)," *Indian Journal of Pharmacology,* 29: 359-365, 1997.
66. Bhattacharya S. et al. "Effects of *Bacopa monniera* on animal models of Alzheimers Disease and perturbed central cholinergic markers of cognition in rats," Res. Comm. Pharn. and Toxicology, 4:1-12, 1999.
67. Dubey et al. *Pharmaco-psychoecologia,* 6:1-5, 1993.
68. Okuyama S. et al. "Effects of VA-045, a novel apovincaminic acid derivative on age-related imparement evidence in electroencephalograph, caudate spindle, a passive avoidance task and cerebral blood flow in rats." *General Pharmacology,* 25 (7): 1311-1320, 1994.
69. Molnar P, Erdo' S L, "Vinpocetine is as potent as phenytoin to block voltage gated Na+ channels in rat cortical neurons." *European Journal of Pharmacology,* 273: 303-306, 1995.
70. Paulo T. et al. "[3H] Noradrenaline-releasing action of vinpocetine in the isolated mail pulmonary artery of the rabbit." *J. Pharm. Pharmacol.* 38: 668-673, 1986.
71. Oyomo E. et al. "Comparison of vinpocetine with ifenprodil tartrate and dihydroergotoxine mesylate treatment and results og long-term treatment with vinpocetine." *Current Therapeutic Research*, Vol. 37 (5): 811-821, 1985.
72. Manconi E. et al. "A double-blind clinical trial of vinpocetine in the treatment of cerebral insufficiency of vascular and degenerative orgin." *Current Therapeutic Research,* Vol. 40 (4): 6702-709, 1986.
73. Balestreri R. et al. "A double-blind clinical trial of the safety and efficacy of vinpocetine in the treatment of patients with chronic vascular senile cerebral dysfunction." *Journal of the American Geriatrics Society,* 35:425-430, 1987.
74. Mizazaki M, "The effect of a crebral vasodilator, vinpocetine, on cerebral vascular resistance evaluated by the dopplar ultrasonic technique in patients with cerebrovascular diseases." *Angiology, The Journal of Vascular Diseases,* 1 (46): 53-58, 1995.
75. Tretter L, and Adam-Vizi, V, "The neuroprotective drug vinpocetine prevents veratridine-induced [Na+] and [Ca+] rise in synaptosomes." *NeuroReport,* 9:1849-1853, 1998.
76. Hindmarch I, et al. "Efficacy and tolerance of vinpocetine in ambulant patients suffering from mild to moderate 76. organic psychodromes." *International Clinical Psychopharmacology,* 6 (1): 31-43, Spring 1991.
77. Subhan Z, and Hindmarch I, "Psychopharmacological effects of vinpocetine in normal healthy volunteers." *European Journal of Clinical Pharmacology,* 28 (5): 567-571, 1985.
78. Coleston D M, Hindmarch I, "Possible memory-enhancing properties of vinpocetine." *Drug Dev. Res.,* 14: 191-193, 1988.
79. *The Merck Index, An Encyclopedia of Chemicals, Drugs, and Botanicals, Twelfth Edition.* Lists multiple, well established structural and functional references with therapeutic use stated as "treatment of memory disorders."
80. Hanin I, et al., "Natural and synthetic Huperzine A: Effect on cholinergic function in vitro and in vivo." *Ann. N.Y. Academy of Science,* 1993; 695, 304.
81. Cheng D, et al., "Huperzine A, a novel promising acetylcholinesterase inhibitor." *Neuroreport,* 8, 1996; 97.
82. Skolnick A A., "Old Chinese herbal medicine used for fever yields possible new Alzheimers disease therapy." *Journal of the American Medical Association,* 277(10): 776, Mar. 12, 1977.
83. Xu, S S. Et al. "Efficacy of tablet huperzine-A on memory, cognition, and behavior in Alzheimer's disease." *Chung Kuo Yao Li Hsuch Pao,* 16(5): 391-395, September, 1995.
84. Qi Xiong Z. et al. "Huperzine-A ameliorates the spatial working memory impairments induced by AF64A." *NeuroReport,* 6, 2221-2224, 1995.
85. Haresh S. et al. "Huperzine-A, a potential therapeutic agent for dementia, reduces neuronal cell death caused by glutamate." *NeuroReport,* 8, 963-968, 1997.
86. Guyton, A. C, *Textbook of Medical Physiology,* 10th Edition, W.B. Saunders Co., 2000.
87. Bagchi, D. et al., "Free Radicals and Grape Seed Proanthocyanidin Extract: Importance in Human Health and Disease Prevention." *Toxicology* 148(2-3): 187-97, 2000.
88. "Iodine May Improve Mental Health." *American Journal of Clinical Nutrition,* 72:1179-1185, 2000.

I claim:

1. A composition for enhanced mental function comprising:
   a. a daily dosage of 20 mcg vitamin B12 on ion exchange resin;
   b. phosphatidyl serine (PS);
   c. a daily dosage of about 200 mg to 300 mg dimethylaminoethanol (DMAE);
   d. a daily dosage of about 30 mg to 60 mg docosahexaenoic acid (DHA);
   e. L-pyroglutamic acid;
   f. herbal extracts from *Bacopa monniera*; and
   g. iodine obtained from a natural source.
2. The composition of claim 1 further comprising at least one antioxidant complex selected from the group consisting of vitamin A, vitamin E, vitamin C and proanthocyanidin.
3. The composition of claim 2 wherein the antioxidant is proanthocyanidin obtained from the grape or the seed of *Vitis vinifera.*
4. The composition of claim 1 further comprising at least one mineral complex selected from the group consisting of calcium, copper, iron, lithium, magnesium, manganese, potassium, vandium and zinc.
5. The composition of claim 4 wherein the mineral complex comprises magnesium, calcium, zinc and iron.
6. The composition of claim 5 wherein the magnesium, calcium, zinc and iron are present as Krebs Cycle Intermediates.
7. The composition of claim 1 wherein the composition further comprises at least one B-complex vitamin selected from the group consisting of vitamin B1, vitamin B2, vitamin B3, vitamin B5 and vitamin B6.
8. The composition of claim 1 further comprising an extract of an herb wherein the herb is selected from the group consisting of *Vinca Minor, Huperzia serrata* and *Vaccinium myrtillus.*
9. A composition for enhanced mental function comprising:
   a. a daily dosage of 20 mcg vitamin B12 wherein the vitamin B12 is on ion exchange resin;
   b. about 30 mg to 100 mg of phosphatidyl serine (PS);
   c. a daily dosage of about 200 mg to 300 mg dimethylaminoethanol (DMAE);
   d. a daily dosage of about 30 mg to 60 mg docosahexaenoic acid (DHA);
   e. about 40 mg to 100 mg of L-pyroglutamic acid;
   f. about 40 mg to 80 mg of herbal extracts from *Bacopa monniera*; and
   g. about 5 mcg to about 100 mcg iodine obtained from a natural source.
10. The composition of claim 9 further comprising at least one antioxidant complex selected from the group consisting of vitamin A, vitamin E, vitamin C and proanthocyanidin.
11. The composition of claim 10 wherein the antioxidant is proanthocyanidin obtained from the grape or the seed of *Vitis vinifera.*
12. The composition of claim 9 further comprising at least one mineral complex selected from the group consisting of calcium, copper, iron, lithium, magnesium, manganese, potassium, vandium and zinc.
13. The composition of claim 12 wherein the mineral complex comprises magnesium, calcium, zinc and iron.
14. The composition of claim 13 wherein the magnesium, calcium, zinc and iron are present as Krebs Cycle Intermediates.
15. The composition of claim 9 wherein the composition further comprises at least one B-complex vitamin selected from the group consisting of vitamin B1, vitamin B2, vitamin B3, vitamin B5 and vitamin B6.
16. The composition of claim 9 further comprising an extract of an herb wherein the herb is selected from the group consisting of *Vinca Minor, Huperzia serrata* and *Vaccinium myrtillus.*
17. The composition of claim 1, wherein the iodine is obtained from kelp.
18. The composition of claim 9, wherein the iodine is obtained from kelp.

* * * * *

UNITED STATES PATENT AND TRADEMARK OFFICE
CERTIFICATE OF CORRECTION

| | | Page 1 of 1 |
|---|---|---|
| PATENT NO. | : 8,329,227 B2 | |
| APPLICATION NO. | : 10/519515 | |
| DATED | : December 11, 2012 | |
| INVENTOR(S) | : Smith | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1013 days.

Signed and Sealed this
Thirtieth Day of December, 2014

Michelle K. Lee
*Deputy Director of the United States Patent and Trademark Office*